(12) United States Patent
Clermont et al.

(10) Patent No.: US 6,667,808 B2
(45) Date of Patent: Dec. 23, 2003

(54) MULTIFUNCTIONAL FOURIER TRANSFORM INFRARED SPECTROMETER SYSTEM

(75) Inventors: Todd R. Clermont, DeForest, WI (US); Francis Jerome Deck, Madison, WI (US); Louie Delaware, Middleton, WI (US); James Ronald Hyatt, Madison, WI (US); George Douglas Jones, Deerfield, WI (US); Gabor John Kemeny, Albuquerque, NM (US); Steven Ralph Lowry, Madison, WI (US); William Joseph McCarthy, Middleton, WI (US); John R. O'Keefe, Madison, WI (US)

(73) Assignee: Thermo Electron Scientific Instruments Corporation, Madison, WI (US)

( * ) Notice: Subject to any disclaimer, the term of this patent is extended or adjusted under 35 U.S.C. 154(b) by 311 days.

(21) Appl. No.: 09/788,855

(22) Filed: Feb. 20, 2001

(65) Prior Publication Data

US 2001/0035957 A1 Nov. 1, 2001

Related U.S. Application Data

(60) Provisional application No. 60/187,678, filed on Mar. 8, 2000.

(51) Int. Cl.[7] .................................................. G01J 3/45
(52) U.S. Cl. ................... 356/451; 356/452; 250/339.08
(58) Field of Search ................................ 356/244, 451, 356/452, 455, 456; 250/339.07, 339.08, 339.09

(56) References Cited

U.S. PATENT DOCUMENTS

| | | | |
|---|---|---|---|
| 3,958,882 A | 5/1976 | Gast | 356/73 |
| 3,977,787 A | 8/1976 | Fletcher et al. | 356/451 |
| 4,387,990 A | 6/1983 | Yazawa et al. | 356/244 |
| 4,415,811 A | 11/1983 | Beck et al. | 250/559.15 |
| 4,784,488 A | * 11/1988 | Doyle et al. | 356/346 |
| 4,786,169 A | * 11/1988 | Brierley et al. | 356/244 |
| 4,799,001 A | 1/1989 | Burch | 318/640 |
| 4,852,955 A | 8/1989 | Doyle et al. | 359/355 |

(List continued on next page.)

Primary Examiner—Edward J. Glick
Assistant Examiner—Therese Barber
(74) Attorney, Agent, or Firm—Foley & Lardner

(57) ABSTRACT

A multifunctional infrared spectrometer system has an interferometer which receives the infrared beam from a source and provides a modulated output beam on beam paths to multiple spatially separated infrared detectors. A multi-position mirror element mounted at a junction position receives the beam on a main beam path and directs it on branch beam paths to sample positions, with the beam then being directed on the branch beam path to one of the detectors. One of the branch beam paths may include a sample holder at the sample position which can index between a position at which a sample is analyzed, to a reference material position, to a pass-through position for calibration purposes. The multi-position mirror element may also be indexed to direct the beam on a branch path to a fiber optic cable which has a probe at the end of it which may be inserted in a sample fluid or powder to be analyzed, with the reflected light from the probe being directed back on an optical fiber cable to a detector at the spectrometer. The multi-position mirror element may be moved to a position at which the beam is directed on a beam path to and through an integrating sphere to a solid sample, with the reflected light from the sample being directed by the surfaces of the integrating sphere to a detector. A detector may be mounted to detect the light transmitted through the sample to obtain measurements of both reflected and transmitted infrared light at the sample.

55 Claims, 13 Drawing Sheets

U.S. PATENT DOCUMENTS

| | | | |
|---|---|---|---|
| 4,882,493 A | * 11/1989 | Lodder et al. | 250/353 |
| 4,991,961 A | 2/1991 | Strait | 356/452 |
| 5,133,598 A | 7/1992 | Badeau | 356/452 |
| 5,184,191 A | * 2/1993 | Krishnan | 356/244 |
| 5,214,277 A | 5/1993 | Drennen, III | 250/216 |
| 5,235,409 A | 8/1993 | Burgi et al. | 356/436 |
| 5,239,361 A | 8/1993 | Burch | 356/345 |
| 5,241,179 A | 8/1993 | Carrieri | 250/341 |
| 5,276,545 A | 1/1994 | Daun et al. | 359/198 |
| 5,319,200 A | 6/1994 | Rosenthal et al. | 250/341 |
| 5,338,935 A | 8/1994 | Truett et al. | 250/339.08 |
| 5,412,473 A | * 5/1995 | Rosencwaig et al. | 356/451 |
| 5,463,223 A | 10/1995 | Wong et al. | 250/339.12 |
| 5,499,095 A | * 3/1996 | Gast et al. | 356/346 |
| 5,537,203 A | * 7/1996 | Carr | 356/236 |
| 5,557,544 A | 9/1996 | Simon et al. | 702/77 |
| 5,585,634 A | * 12/1996 | Stevenson et al. | 250/339.11 |
| 5,760,399 A | 6/1998 | Trygstad | 250/339.07 |
| 5,815,045 A | * 9/1998 | Koyanagi et al. | 250/339.12 |
| 5,883,712 A | 3/1999 | Coffin | 356/346 |
| 5,896,197 A | 4/1999 | Coffin | 356/346 |
| 5,923,039 A | 7/1999 | Jablonski et al. | 250/373 |

* cited by examiner

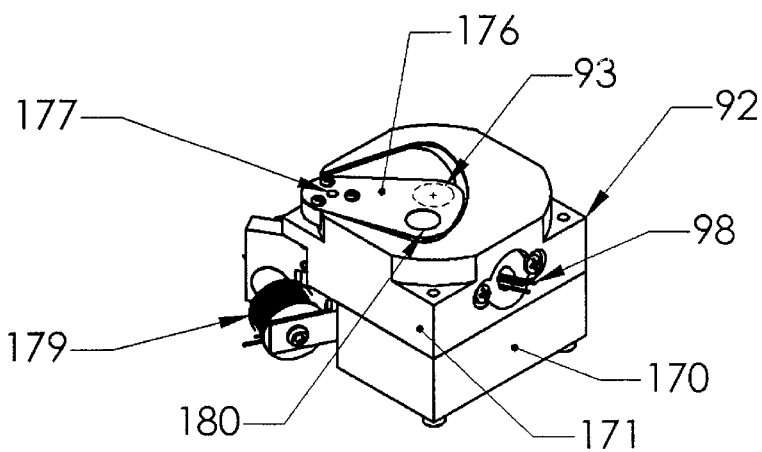
FIG. 12
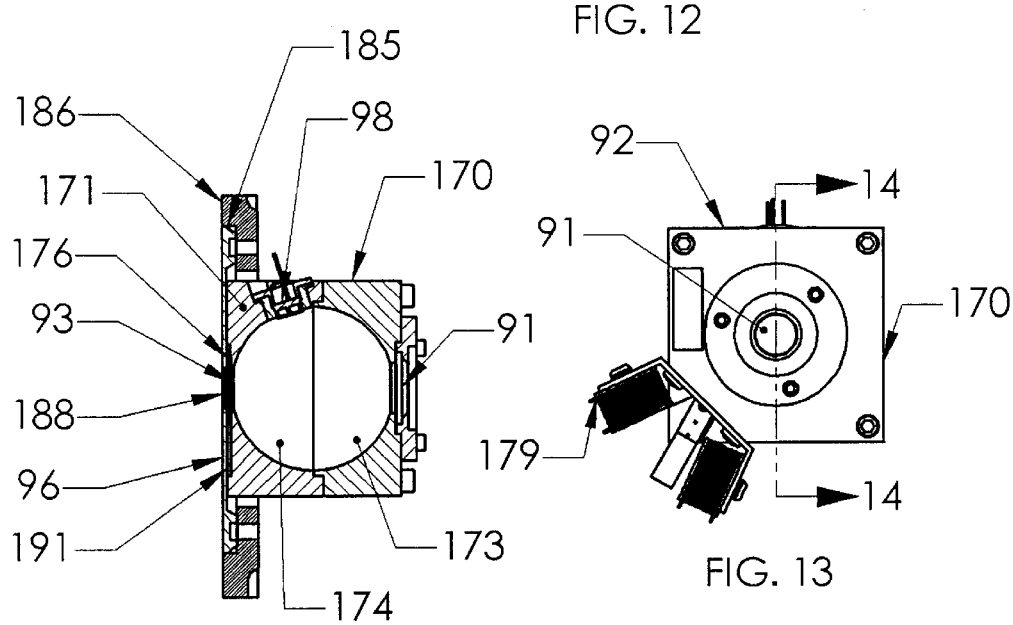
FIG. 14
FIG. 13
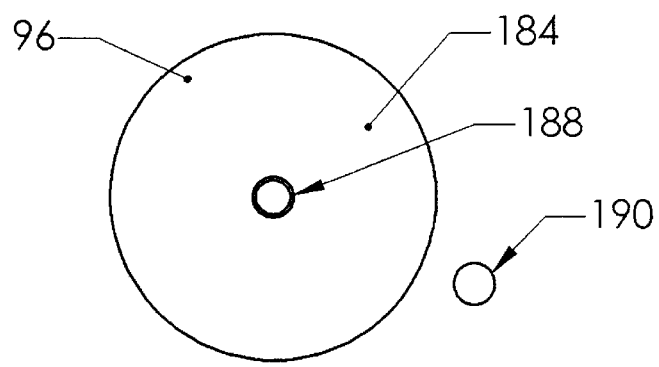
FIG. 15

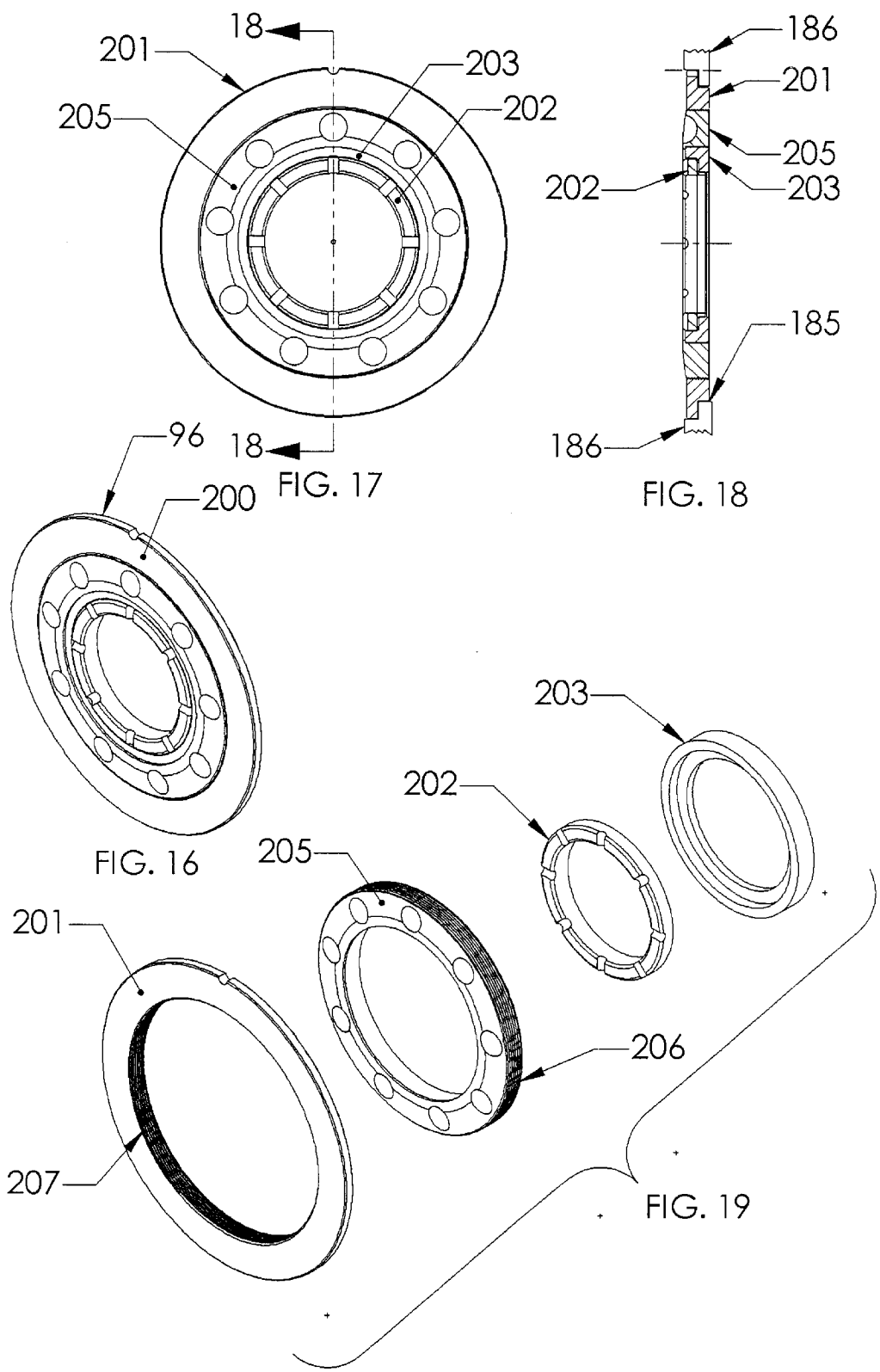

MULTIFUNCTIONAL FOURIER TRANSFORM INFRARED SPECTROMETER SYSTEM

REFERENCE TO RELATED APPLICATION

This application claims the benefit of provisional patent application No. 60/187,678, filed Mar. 8, 2000, the disclosure of which is incorporated by reference.

FIELD OF THE INVENTION

This invention pertains generally to Fourier transform infrared spectrometers and to sample holders for such spectrometers.

BACKGROUND OF THE INVENTION

Fourier transform infrared (FTIR) spectrometers are utilized to perform accurate and efficient identification of the chemical composition of a sample. Such spectrometers typically incorporate a Michelson interferometer having a moving mirror. The interferometer modulates the infrared beam from an infrared source to provide an output beam in which the intensity of the infrared radiation at various wavelengths is periodically varied. The output beam is focused and passed through or reflected from a sample, after which the beam is collected and focused onto a detector. The detector provides a time varying output signal which contains information concerning the wavelengths of infrared absorbance or reflectance of the sample. Fourier analysis is then performed on the output signal data to yield usable information on the chemical composition of the sample.

Conventional FTIR spectrometers include a sample chamber in which a sample is held in a position to be exposed to the infrared beam from the spectrometer. The sample which is to be analyzed may take various physical states, i.e., a liquid, solid or gas, and solid samples may have various physical characteristics. For example, a solid material to be analyzed may be in the form of a block or sheet of material (e.g., polymer plastics), in the form of powders or granulates, or in specific formed shapes (e.g., pharmaceutical tablets, pills and capsules).

The conventional manner of analyzing these various materials has been to prepare the sample so that it is in a form that can be accepted by the sample holder in the sample chamber of the FTIR spectrometer. For example, for a bulk liquid a small sample of the liquid may be transferred to a small cuvette or other container which is then mounted in the sample holder in the sample chamber. For bulky solid materials, small shavings or particles may be removed from the bulk sample, appropriately prepared (e.g., ground, pulverized, etc.) and placed in a sample holder which can then be inserted into the sample chamber. Other materials may be reduced to a powder which can be held in the sample holder or may be dissolved in a solvent which is then transferred to a cuvette or tube of an appropriate size to be mounted in the sample holder. Such conventional sample preparation techniques may not always be feasible or desirable, and specialized spectrometry equipment has been developed for specialized applications. These include probes, connected by fiber optic cables to a spectrometer, that can be inserted into a liquid, solid powder, or gas to be sampled (e.g., a flowing material where composition information is to be gathered for process control).

Another particular specialized use of spectroscopy equipment is in the pharmaceutical industry. The finished pharmaceuticals are usually in a specific shape, e.g., as pills, tablets, or caplets, some of which may be coated or printed with markings, as well as powder filled hard gel capsules and soft gel capsules having active ingredients suspended in water-free media surrounded by a soft gelatin shell. Classical wet chemistry methods and liquid and gas chromatographic techniques were traditionally used in the pharmaceutical industry to analyze the chemical composition of the finished pharmaceuticals. These methods require chemicals such as solvents, indicators, derivitizing agents, and chromatographic mobile phase solvent mixtures. The use of such chemicals requires specialized facilities and trained personnel, and involves fire and toxicity hazards. Such procedures involve not only the expense of the materials themselves but also the expense of their safe disposal after the analysis is done. For these reasons, nondestructive analysis techniques are increasingly being used for analysis of pharmaceuticals, as well as other compounds. One of the most widely used nondestructive techniques is near-infrared spectrographic analysis. The near-infrared region, generally in wavelengths from about 666 nm to 3333 nm, has been found to be particularly suitable for such nondestructive analysis because of its penetration depth into a pharmaceutical sample. Using near-infrared light, the sample can be analyzed in a reflectance mode or a transmittance mode.

The reflectance mode obtains information from the illuminated surface of the sample. The infrared light reflects from the surface of the sample and from shallow layers beneath the surface. Due to absorption and scattering, most of the information in the reflected light received by the detector is dominated by the composition of the surface layers, such as the coatings of pharmaceutical tablets. Some coating films are made with near-infrared transparent (e.g., modified cellulosic) materials such that the active substances in the tablet are readily detected in reflectance mode without much distortion. Other pharmaceutical formulations have coatings that have color additives or scattering materials, such as $TiO_2$, talc, $CaCO_3$, etc., that hinder the light from adequately reaching the interior of the tablets. In any event, the reflectance mode is sensitive to variations of the coating thickness and of the composition of the coating material. Further, if a tablet being analyzed is imprinted with ink, the spectral signature of the ink will be detected (which can be shown by comparing analyses of the printed and unprinted side of the tablet). A particular disadvantage of the reflectance sampling mode is that because the interior of the tablet is not readily analyzed, the overall dosage of the tablet cannot be directly quantified. Further, the repeatability of the optical reflectance measurement is affected by the angular position of any imprint pattern on the sample, which may vary from tablet to tablet. Thus, it is often desirable to transmit the near-infrared light through the tablet and analyze the transmitted light in addition to or as an alternative to reflectance measurements. Specialized spectrometry equipment, including specialized sample holders, have been developed for the analysis of pharmaceutical samples in the reflectance mode and in the transmission mode, but generally such equipment is not well suited to carry out both reflectance and transmission measurements on the same sample.

SUMMARY OF THE INVENTION

In accordance with the invention, a multifunctional infrared spectrometer system is capable of performing transmission or reflection measurements, or both, on a variety of samples, including liquids and powders as well as shaped solid samples such as pharmaceutical pills and tablets. The various samples can be tested utilizing the same spectrometer system without modification of the spectrometer and without the addition or rearrangement of sample compartments and sample holders. Preferably, the spectrometer system includes a sample position at which a sample may be mounted in a sample holder for transmission of a modulated infrared beam through the sample, while a sample may be analyzed at a second sample position using a probe connected by fiber optic cables to the spectrometer to analyze samples remote from the spectrometer, while at a third sample position a shaped solid sample such as a pharmaceutical tablet may be analyzed in reflection, transmission, or both. The spectrometer system is adapted to easily and quickly switch between sample positions under the command of the operator by simple commands without requiring the attachment or removal of auxiliary sample compartments or holders.

The multifunctional infrared spectrometer system of the invention includes a source of infrared radiation that provides a beam of infrared, an interferometer which receives the beam from the source and produces a modulated output beam, at least two spatially separated infrared detectors, optical elements transmitting the modulated output beam from the interferometer on a main beam path to a junction position, and optical elements defining a first branch beam path from the junction position to a first sample position and then to a first of the detectors, and optical elements defining a second branch beam path from the junction position to a second sample position and then to a second of the detectors. A multi-position mirror element is movable between at least two positions. In a first position of the mirror element, the beam on the main beam path is passed on the first branch beam path to the first sample position and thence to the first detector, wherein in a second position of the mirror element, the beam on the main beam path is passed on the second branch beam path to the second sample position and thence to the second detector. A third infrared detector may also be provided in the system which is separated from the other detectors, with optical elements defining a third branch beam path from the junction position to a third sample position and thence to the third detector, with the multi-position mirror element then movable to a third position in which the mirror element passes the beam on the main beam path on the third branch beam path to the third sample position and thence to the third detector. The multi-position mirror element is controlled by the operator preferably under software control to index to the desired position to direct the infrared beam to the desired sample position, thereby allowing different types of samples and different types of sample holders and sampling components to be used with the same spectrometer without modification of the spectrometer.

Preferably, one of the branch beam paths includes a sample holder which has a sample port at which a sample may be mounted in a conventional tube, film or cuvette for transmission of the infrared beam through the sample port and the sample to a detector. The sample holder also preferably has a reference port at which a reference material may be mounted for transmission measurements and a pass-through port which is completely open. The sample holder may be mounted on a carriage that can be indexed to move the sample holder from position to position such that the infrared beam may be passed through the sample port, or the reference port, or the pass-through port at the command of the operator. The sample holder may be heated and the temperature of the holder controlled to control the temperature of the sample and reference material as desired. By indexing the sample holder to a position at which the infrared beam passes unimpeded through the pass-through port, baseline calibration measurements can be made of the unimpeded beam path to the detector. By indexing the holder such that the infrared beam passes through the reference port, a reference spectra can be taken from a known material and the spectra thereby obtained compared to the known spectra of the reference material to allow calibration of the system.

A second of the branch beam paths may include a supply optical fiber cable which directs the beam to a probe tip at which the infrared may be projected onto and reflected from a sample (or transflected by transmission to a reflector and back through the sample), such as a bulk fluid. The infrared reflected or transflected from the sample material (e.g., the fluid in which the probe is immersed) is received at an inlet end of an optical fiber return cable which directs the reflected light back to a detector at the spectrometer. The spectrometer system may include a cradle unit with an open socket in which an elongated tube of the probe may be inserted when the probe is not being used. The cradle unit preferably includes a stop member with a reflecting member therein to which the probe tip is engaged when the probe is fully inserted into the receptacle of the cradle unit. A sensor is mounted to sense the presence of a probe tip adjacent to the stop member. The spectrometer can then automatically carry out a calibration measurement by directing infrared through the supply optical fiber cable to the reflecting member and directing a reflected light back through the return optical fiber cable to the detector to allow a baseline calibration to be made of the probe without a sample.

In a third of the branch beam paths the beam may be directed through the inlet of an integrating sphere and thence to the outlet of the integrating sphere through a window to impinge upon a solid sample, such as a pharmaceutical pill, held at a sample position on the window. The infrared light reflected from the sample passes back into the integrating sphere and is diffusely reflected from the walls of the sphere to a detector mounted in the integrating sphere. Another infrared detector is preferably mounted on the other side of the sample position from the window to detect infrared light transmitted through the sample. A shield is preferably mounted to engage the periphery of the sample, such as a tablet, to prevent the infrared light from passing around the periphery of the tablet into the detector. For round pills, a shield may be used which includes an adjustable iris having a circular inner periphery of adjustable diameter which can be narrowed down to engage to the outer periphery of a circular tablet and thus be utilized with circular tablets of various sizes. For calibration of the reflected light detector in the integrating sphere, a flip panel is preferably mounted between the outlet opening of the integrating sphere and the window which can be indexed between a position in which the infrared light is passed from the outlet opening to the sample to a position in which the flip panel blocks the infrared light exiting from the outlet opening. The flip panel then reflects the light diffusely back into the integrating sphere so that calibration measurements on the beam path to the integrating sphere detector may be obtained.

A further preferred feature of the invention includes a replaceable source having a source housing with a source enclosure to which a replaceable source element may be mounted. The source housing has an outward flange adapted to engage against a surface of the spectrometer enclosure and to be fixed precisely in location by a pin extending from the flange which is inserted into a slot or opening in the spectrometer enclosure. The replaceable source element includes electrical contact pads electrically connected to the source element that are mounted on the source housing in a position to be engaged with electrical contacts on the spectrometer enclosure to make electrical contact when the source housing is mounted into the enclosure. The source element can be readily replaced by an operator by removing the source housing from the enclosure, and then replacing the source housing in its precisely indexed position so that the source element itself is precisely located with respect to the optical elements in the main beam path of the spectrometer.

Further objects, features and advantages of the invention will be apparent from the following detailed description when taken in conjunction with the accompanying drawings.

BRIEF DESCRIPTION OF THE DRAWINGS

In the drawings:

FIG. 12 is a perspective view of the exterior of an integrating sphere unit in accordance with the invention.

FIG. 13 is a bottom plan view of the integrating sphere unit of FIG. 12.

FIG. 14 is a cross-sectional view of the integrating sphere unit taken generally along the lines 14—14 of FIG. 13.

FIG. 15 is a plan view of an exemplary shield for use with a tablet of a specific size and shape in conjunction with the integrating sphere unit.

FIG. 16 is a perspective view of another shield having an adjustable iris for use with the integrating sphere.

FIG. 17 is a plan view of the adjustable iris shield of FIG. 16.

FIG. 18 is a cross-sectional view of the adjustable iris shield taken generally along the lines 18—18 of FIG. 17.

FIG. 19 is an exploded view of the adjustable iris shield of FIG. 16.

DETAILED DESCRIPTION OF THE INVENTION

Figure 1:
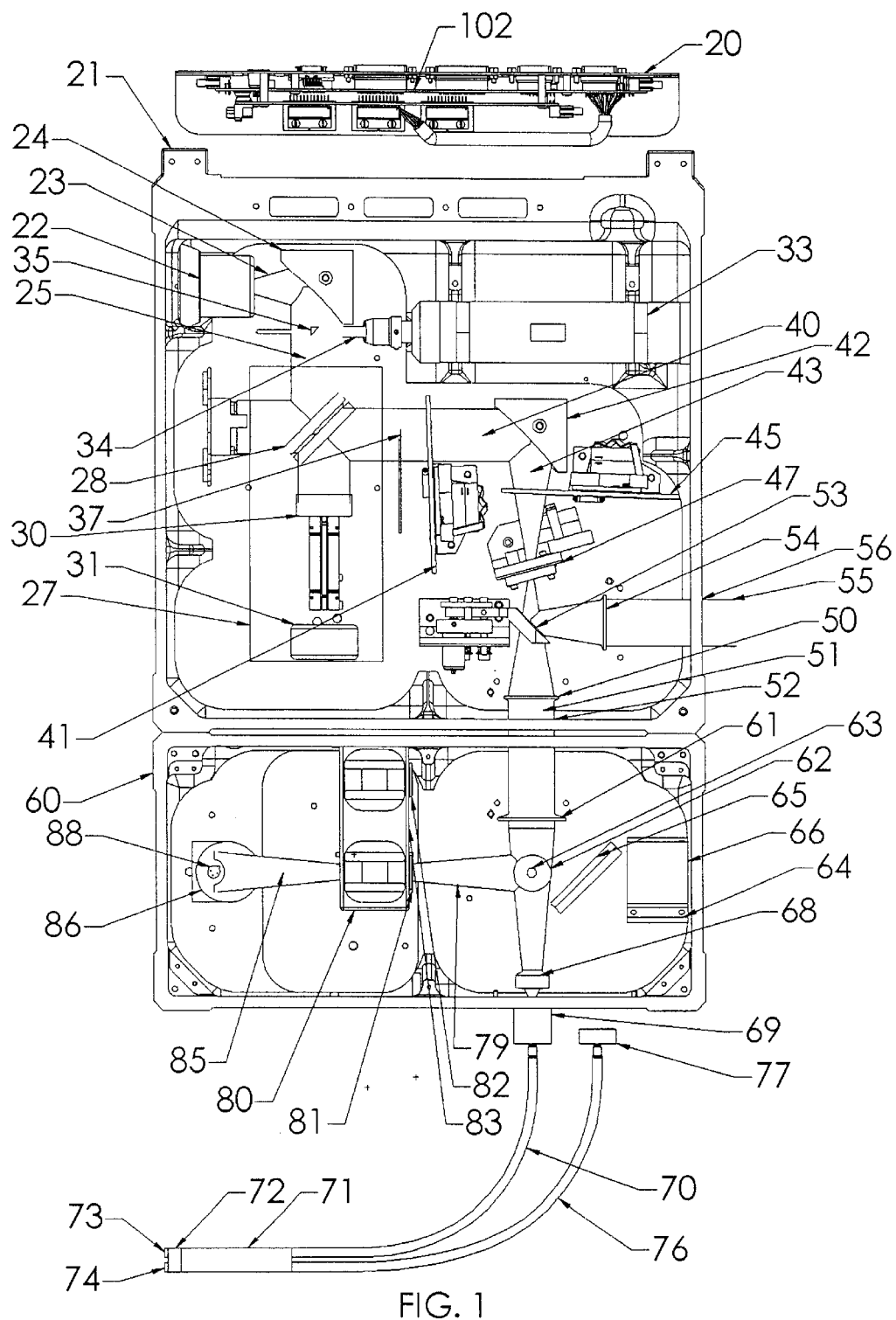
FIG. 1 is a schematic diagram of the optical elements of the multifunctional infrared spectrometer system of the invention.

With reference to the drawings, the multifunctional FTIR spectrometer system of the invention is shown generally in schematic form at 20 in FIG. 1 for purposes of illustrating the principles of the invention. Within a basic spectrometer enclosure 21 is mounted a near-infrared source 22 which provides an (e.g., diverging) output beam 23 that is collected and collimated by a first mirror 24. The collimated beam 25 from the mirror 24 is passed into an interferometer 27 composed of a beam splitter 28, a fixed mirror 29, and a moving mirror 30. The moving mirror is driven in reciprocating motion toward and away from the beam splitter 28 by a mounting and driving mechanism 31. A laser 33 (e.g., a HeNe laser at 632.8 nm) provides a monochromatic output beam 34 to a small mirror 35 which directs the beam into the beam splitter 28. The laser beam after passing through the interferometer is directed to a detector 37, which measures the interference fringes of the laser beam to allow the moving mirror position to be determined in a conventional manner. The fixed mirror 29 may be mounted for precision dynamic adjustment of its position in a conventional manner. Such interferometers are well known and any desired interferometer system may be utilized for the interferometer 27. Although a Michelson type interferometer system is generally preferred, other types of interferometers may be used. Examples of interferometer systems and mirror alignment mechanisms for interferometers are described in U.S. Pat. Nos. 4,799,001, 4,991,961, 5,133,598, 5,239,361, 5,276,545, 5,883,712 and 5,896,197.

The output beam 40 exiting from the interferometer 27 is modulated by the interferometer in a known time varying manner. The output beam 40 is preferably collimated, as shown in FIG. 1 and is passed on a main beam path through a first attenuator wheel 41 which has multiple positions for holding attenuator material of various types as discussed below, as well as a direct pass-through position through which the beam can pass unimpeded. After passing through the wheel 41, the collimated beam 40 is incident upon a focusing mirror 42 which directs a converging beam 43 on the main beam path through a second filter wheel 45 which again has multiple positions which contain filter material and reference material, as described further below, as well as an open position for allowing direct pass-through of the focusing beam 43. The beam 43 is brought to a focus at the aperture of a J-stop mechanism 47. The aperture provided by the J-stop 47 spatially defines the radiating beam of infrared light and further blocks stray light from further transmission through the system, particularly back to the interferometer 27. It is preferred that the J-stop 47 be mounted in the position shown, i.e., at a position after the infrared beam has passed through the interferometer, rather than in the conventional position prior to the interferometer, because of the blocking by the J-stop 47 of stray light that may be introduced by optical elements in the main beam path. Preferably, the J-stop 47 provides an adjustable aperture in a conventional manner, e.g., having an adjustable iris driven by a stepper rotor under control of the controller 102.

After passing through the aperture of the J-stop 47, the now-diverging beam 43 is received by a collimating lens 50 which forms a collimated beam 51 that is directed on the main beam path through an outlet opening 52 in the enclosure 21. Optionally, a movable deflecting mirror 53 may be mounted adjacent to the diverging beam between the J-stop 47 and the collimating lens 50. The mirror 53 is mounted so that it can be moved laterally or rotated into place, either manually or by a motor drive, into the diverging beam 43 to direct it to another collimating lens 54 which directs a collimated beam 55 through a second outlet opening 56 to other instrumentation (not shown). When not in use, the outlet opening 56 is generally preferable capped to close it off to help maintain an environment within the enclosure 21 that is sealed off from the ambient atmosphere.

After exiting through the outlet opening 52, the beam 51 passes on the main beam path into a sample compartment enclosure 60. Although a separate sample compartment enclosure 60 and spectrometer enclosure 21 are illustrated, it is understood that a single enclosure may be utilized. In the enclosure 60 the beam 51 is received by a focusing lens 61 which provides a converging beam 62 that is directed on the main beam path toward a junction position 63. As discussed above, the mirror 42 and the lenses 50 and 61 are the optical elements that define the main beam path from the interferometer to the junction position 63. It is understood that focussing mirrors may be used rather than lenses, and that any desired transmissive or reflective optical elements may be used to form the beam path. A multi-position mirror element 64 is mounted for translation toward and away from the position 63 and includes a laterally diverting mirror 65 and an upwardly diverting mirror 66 disposed laterally of the mirror 65. Both mirrors may be flat mirrors with surfaces in planes that are non-parallel to each other, with each mirror plane intersecting the axis of the main beam path at the junction position of an acute angle. The mirror element 64 has at least two and preferably three positions. Although these positions are described below as first, second and third positions, it is understood that the positions may be used in any order, and any one of the positions may be the first position or the second position or the third position. In a first of the positions, shown in FIG. 1, the laterally deflecting mirror 65 and the upwardly deflecting mirror 66 are both out of the path of the beam 62, which then passes on a branch beam path (transmitted through air as the optical element) to a focusing lens 68 which focuses the beam onto an opening of a fiber optic coupler 69. The fiber optic coupler 69 is adapted to be connected to an optical fiber supply cable 70 which directs the infrared light to a probe 71 having a probe tip 72 at which the illuminating light exits at an outlet end 73. The probe tip 72 also has an inlet end 74, for receiving light reflected from a sample, which is coupled to an optical fiber return cable 76 which may be connected to an infrared detector 77. The cables 70 and 76 are flexible and allow the probe 71 to be used to sample materials at a position remote from the spectrometer, e.g., by inserting the probe tip into a fluid or powder to allow measurements of the composition of the sample.

The mirror element 64 may be indexed to a second position, e.g., in which the laterally deflecting mirror 65 is inserted into the converging beam 62 at the junction position 63. The mirror 65 then serves to deflect the beam 62 into a converging beam 79 on a second branch beam path to a sample holder 80. As discussed further below, the sample holder 80 preferably has multiple positions to allow the converging beam 79 to be incident upon a sample port 81 in the holder 80, or on a reference port 82 in the holder, or on an open pass-through port 83 through which the beam passes unimpeded. The light that passes either through the sample port, the reference port, or the open port 83 forms a beam 85 which is incident upon a focusing mirror 86 that focuses the beam upwardly onto an infrared detector 88. In this second position of the mirror element 64, transmission measurements through a sample held at the sample port 81 can thus be obtained.

Figure 2:
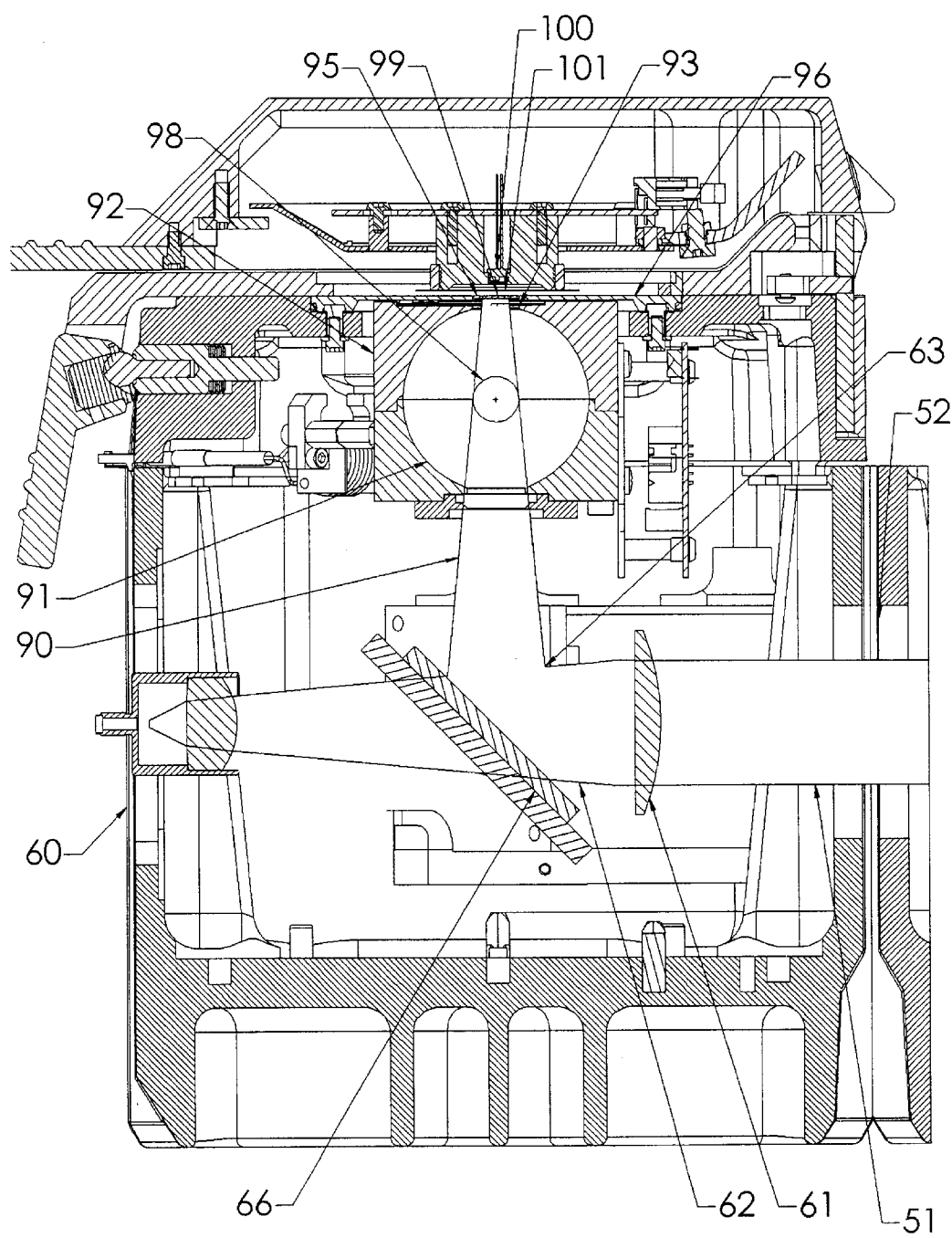
FIG. 2 is a schematic diagram of the optical elements in the spectrometer system taken generally from the right-hand side of FIG. 1.

In a third of the positions of the mirror element 64 it is translated laterally to a position in which the upwardly deflecting mirror 66 is interposed into the main beam path converging beam 62 at the junction position 63. As best shown in FIG. 2, which is a schematic view taken from the right side of FIG. 1, the converging beam 62 when intercepted by the mirror 66 is deflected upwardly on a third branch beam path into a converging beam 90 that passes through an inlet opening 91 of an integrating sphere 92 and thence through an outlet opening 93 of the integrating sphere to a sample 95 (e.g., a pharmaceutical pill, tablet, capsule, etc.) that is held within a shield 96. Incident light that is reflected from the sample 95 is diffusely reflected from the surfaces of the integrating sphere 92 until incident upon an infrared detector 98 mounted in the sphere 92 which detects the reflected light in the sphere from the sample 95. Generally, the sample 95 will not be entirely opaque to the light of the incoming beam 90, and a portion will pass therethrough in transmission in a converging beam 99 and will be incident upon a transmitted light detector 100. The shield 96 preferably closely engages the outer periphery of the sample 95 to minimize stray light passing around the sample 95 to the detector 100. Further, a spatial element 101 is preferably mounted adjacent to the detector 100 or forms a part thereof to restrict the spatial aperture of the light transmitted through the sample 95 in the converging beam 99 to the detector 100, and thereby minimize the incidence of stray light onto the detector 100. Thus, in this third indexed position of the mirror unit 64, reflection and transmission measurements of the same sample 95 may be carried out, sequentially or simultaneously, without moving the sample.

A system controller 102, shown schematically in FIG. 1, is connected to the various components described above to control them using conventional control techniques. The controller 102 preferably includes a computer and/or digital signal processor and conventional input and output devices.

Figure 3:
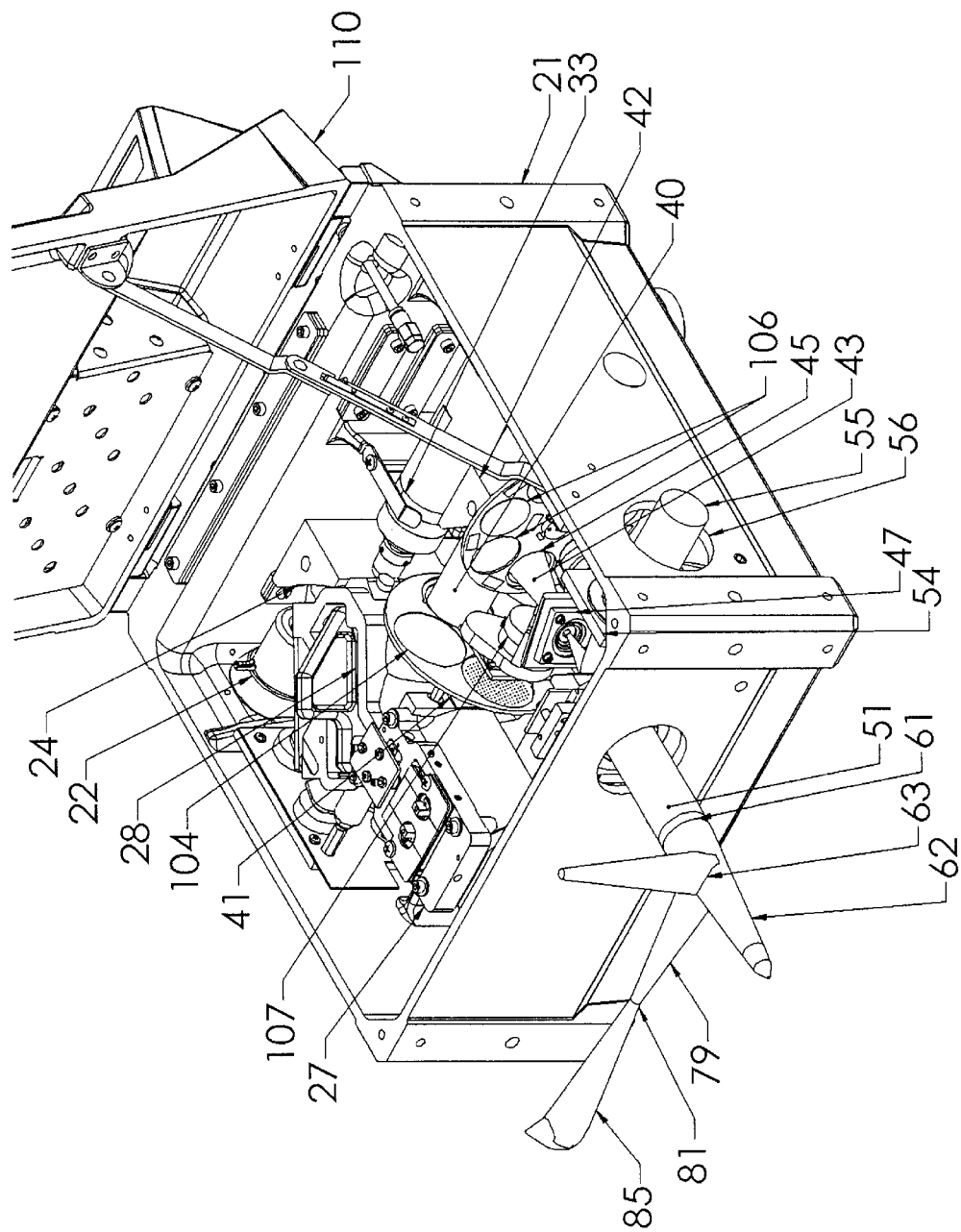
FIG. 3 is a more detailed perspective view of a preferred infrared spectrometer enclosure with spectrometer components therein in accordance with the invention.

More detailed views of an exemplary implementation of the multifunctional spectrometer of the invention are shown in FIGS. 3–6. With particular reference to FIG. 3, the attenuator wheel 41 has several openings 104 formed therein in which may be mounted discs of various materials. For example, one opening may have a conventional metal screen (e.g., etched sheet metal coated with black oxide) therein providing approximately 10% transmission therethrough, a second opening may have a metal screen providing approximately 3% transmission, and a third opening may have a disc of polystyrene or other material (typically mounted with a metal screen having 3% or 10% transmission) therein as a reference material for wavelength accuracy monitoring. One of the openings 104 is open so that the beam 40 can pass therethrough unimpeded. The purpose of the attenuators in the wheel 41 is to appropriately attenuate the beam sufficiently to avoid saturation of the detectors. Similarly, the filter wheel 45, if utilized, has a series of openings 106 in which may be mounted filter discs of various materials while one of the openings 106 is left open to allow impeded passage of the converging beam 43 therethrough. As an example, the openings 106 may have discs therein of neutral density glass or other transmissive material (e.g., metallic coated calcium fluoride, metallic coated borosilicate glass, etc.) providing various levels of transmission, e.g., 2%, 10%, 20%, 40% and 80%, along with a disc of polystyrene or other material that is a reference material for wavelength accuracy measurements. The filter wheel 41 is driven to index from position to position by a drive motor 107 which is controlled by the system controller, and the filter wheel 45 is driven in rotation to index from position to position by a drive motor 108, again under the control of the system controller. Filter wheels of this type are conventionally used in infrared spectrometers. The purpose of such wheels is to allow controlled attenuation of the illumination beam. For example, each of the openings 104 in the wheel 41 (except the pass-through opening) may have screen discs mounted therein which are selected to have a large amount of infrared attenuation and are used to provide attenuation during background measurements with no sample in the beam path. The openings 106 in the filter wheel 45 (except for the pass-through opening) may have disks formed therein which have relatively wide differences in infrared attenuation and can be used for measurements for quantifying the constituents of a sample. Preferably, one of the openings in the wheel 41 (or the wheel 45 or both) has a disc therein of a selected reference material, e.g., polystyrene, which has known spectral peaks. Thus, by interposing the disc with the material of known spectral response into the beam path (which is otherwise unimpeded between the interferometer and the selected detector) the spectral response obtained from the detector can be compared with the known response that should be obtained from the known material in the wheel, thus allowing the positions of the spectral peaks in the detected signal to be calibrated or monitored.

Figure 4:
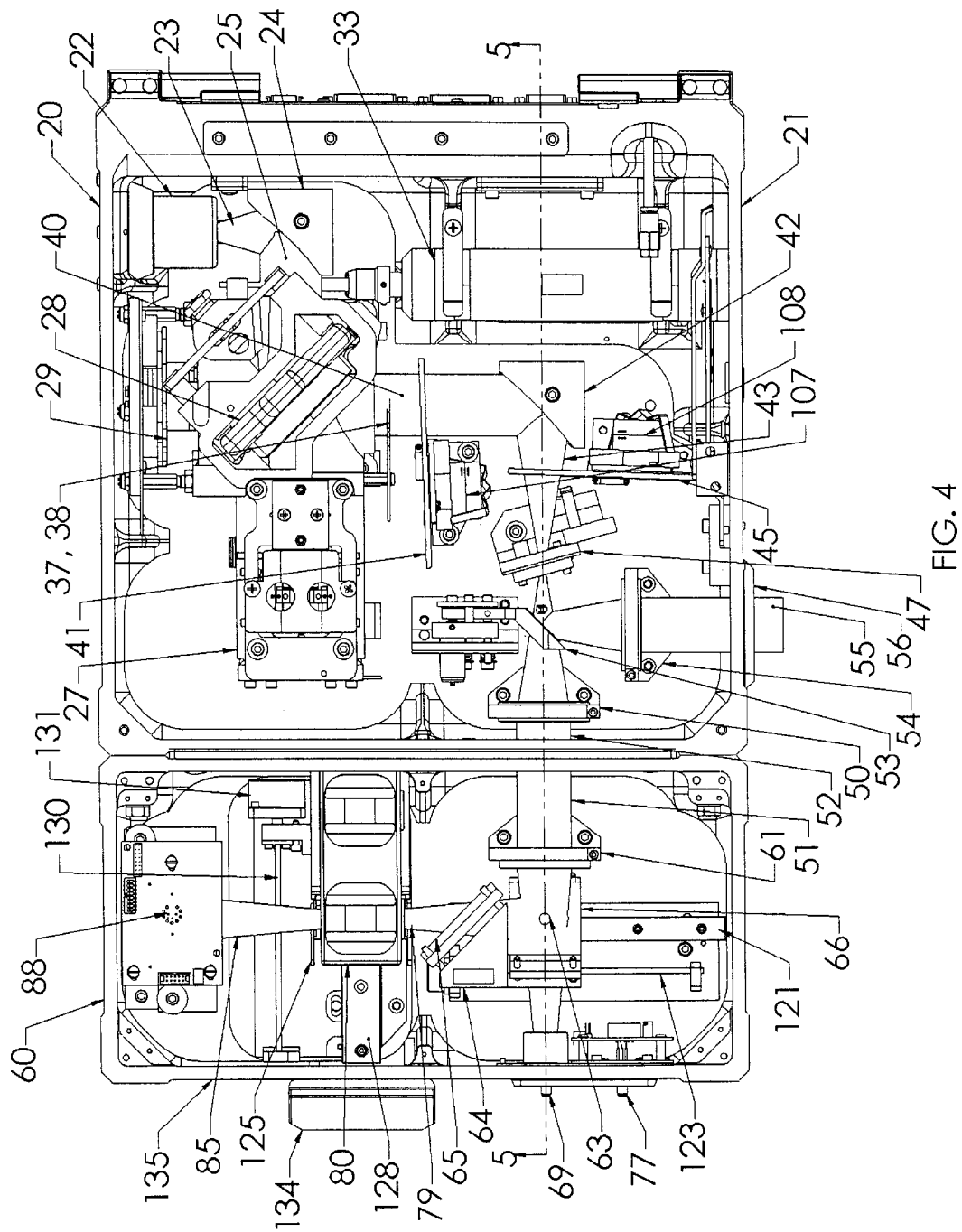
FIG. 4 is a more detailed plan view of the multifunctional infrared spectrometer system of the invention.

As shown in FIG. 4, the wheels 41 and 45 and the J-stop aperture unit 47 (as well as other elements in the beam path) may be mounted so that they face the optical axis of the main beam path at an angle off of normal to thereby minimize stray reflection back to the interferometer.

As illustrated in FIG. 3, the enclosure 21 for the spectrometer compartment may include a cover 110 which is hinged to open and close and, when closed, covers the optical elements within the spectrometer enclosure. The cover 110 may also have the electronic control components of the controller mounted thereto and may provide user interface components on its outer surface.

As discussed further below, the source 22 is preferably formed to be readily removable from and inserted into the enclosure 21 and to seat in a position precisely aligned with the mirror 24 so that no alignment is required by an operator after the source is reinstalled. The source preferably provides an output beam 23 which includes wavelengths in the near infrared range, e.g., from about 666 nm to 3333 nm, although the spectrometer of the invention may be utilized with other sources and other wavelengths. The optical elements of the system are chosen to suit the wavelength range utilized. For use with near infrared illumination, the beamsplitter 28 and the lenses 50, 54, 61 and 68 may be formed of calcium fluoride ($CaF_2$). The mirrors may be formed in a conventional fashion, e.g., by diamond turned machining of aluminum blocks, and may be plated or coated with conventional materials, e.g., gold, silver, etc. For detection of near infrared light, suitable detectors 77, 88, 98 and 100 are InGaAs infrared detectors available commercially from various sources such as EG&G.

Figure 6:
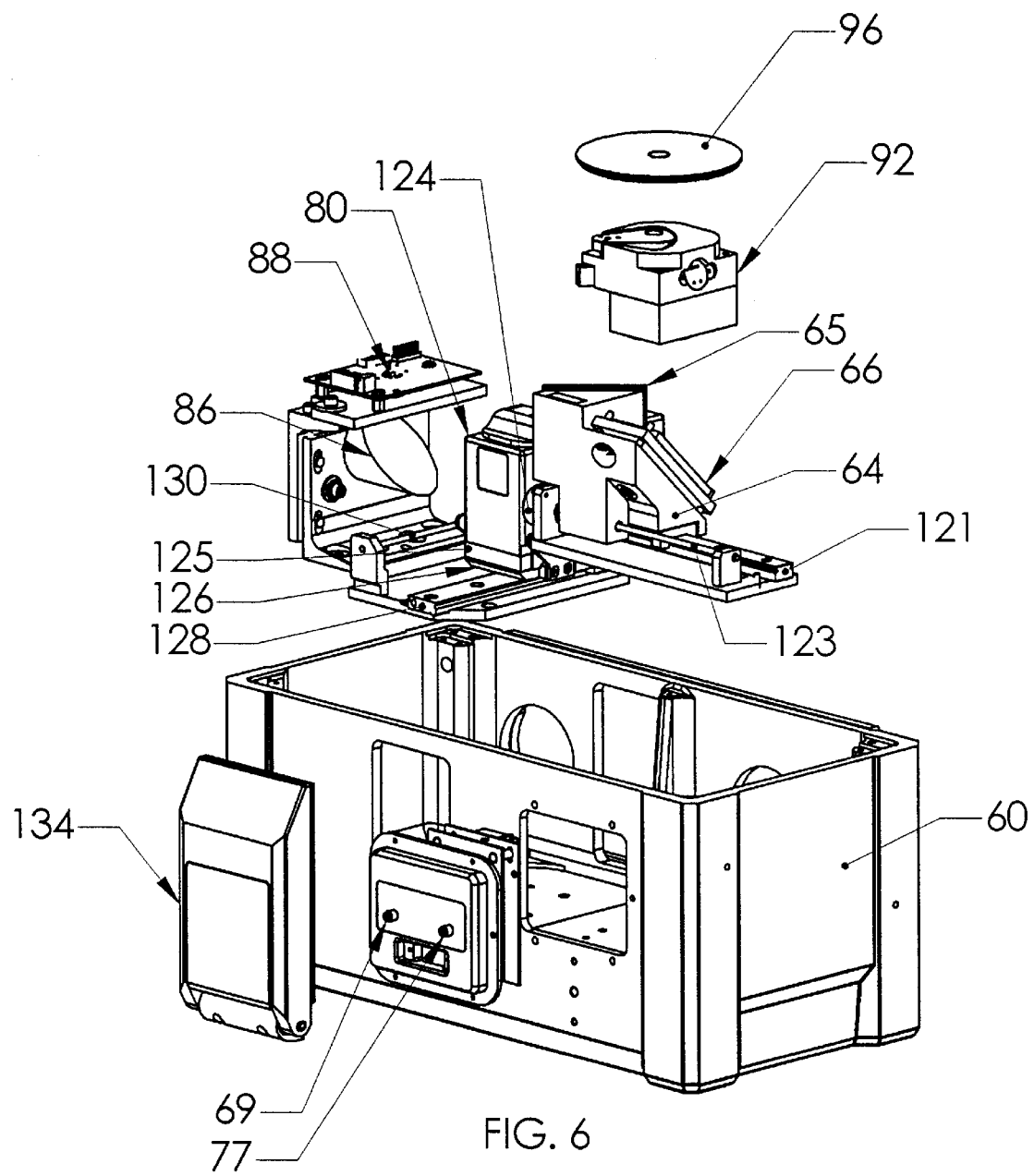
FIG. 6 is a partially exploded view of the components of the sample compartment enclosure of the spectrometer system of the invention.

As best shown in FIG. 6, the mirror element 64 is mounted for lateral motion on a slide 120 which slides on a rail 121. The mirror element 64 is driven laterally to index the mirrors 65 and 66 to their appropriate positions by a jack screw 123 rotated by an electric stepper motor 124 which is supplied with power from the system controller.

As also illustrated in FIG. 6, the sample holder 80 is mounted on a carriage 125 which is itself mounted on a slide bearing 126 which is mounted for sliding motion to a rail 128. The carriage 125 is connected to a jack screw 130 which is driven in rotation by an electric stepper motor 131 which is supplied with power from the system controller. When a sample is to be changed, the system controller provides power to the motor 130 to drive the carriage 125 with the sample holder 80 supported thereon outwardly toward a spring-loaded door 134. The door 134 is driven open by the carriage 125 as it engages the door such that the carriage and the sample holder 80 supported thereon extend partially outwardly from an outer wall 135 of the sample chamber to allow access to the sample holder 80 by an operator.

The sample holder 80 is shown in more detail with reference to FIGS. 7–11. The holder 80 has three ports, a sample port 81 for the sample to be tested, a central open port 83 which is a straight pass-through to allow unimpeded passage of the beam 79, and a reference port 82 at which a reference material may be positioned to obtain reference measurements. The carriage 125 can be moved under control of the operator, or automatically, to index the position of the sample holder 80 until either the port 81, the port 83 or the port 82 is in the path of the beam 79. Each of the ports 81, 82 and 83 may be spatially defined by aperture plugs 140 which provide a (preferably identical) precisely limited circular aperture for the beam that will be incident upon the sample, etc. Such aperture plugs are preferably used with sample holding tubes which have a smaller diameter than that of the beam at the sample position. The aperture plugs are mounted in a front face 141 of a rectangular enclosure body 142 of the sample holder. A back face 143 of the enclosure body has openings 144, 145 and 146 therein to allow passage therethrough of the beams that were incident upon the ports 81, 83 and 82, respectively. Openings in the enclosure body above the sample port 81 and the reference port 82 are closed by cover plugs 148 and 149, respectively. The enclosure body 142 and the cover plugs 148 and 149 may be formed of any suitable structural material, for example, of polyetherimide plastic. To facilitate proper registration of a cuvette or tube holding a sample within the sample holder, as best shown in the cross-sectional view of FIG. 10, the receptacle for the sample in the holder includes a front panel 151, with an opening in it at the port 80, and a pressure plate 152 which is pressed up against the panel 151 by springs 153. The pressure plate is held in position by engagement with a pin 155 and has a central opening 156 therein that aligns with the inlet port 81. When a new sample is to be inserted in place in the sample compartment, the cover plug 148 is removed, the present sample tube, vial or cuvette, etc., if any, is removed from the sample receptacle by the operator, and a new tube, vial or cuvette is inserted between the front plate 151 and the pressure plate 152, pushing the pressure plate outwardly against the force of the springs 153 until the sample tube engages the bottom 154 of the enclosure body. The pressure plate 152 thus tightly holds the sample tube, vial, cuvette, etc. tightly in place against the aperture plug 140 to provide accurate placement of the sample with respect to the focussed beam 79 and to minimize the chance of any stray light from the beam passing around the sample. A reference receptacle is formed by a similar pressure plate 152, springs 153, and pin 155, mounted in the compartment under the cover plug 149 to allow a tube or vial, etc. containing the reference material to be inserted in proper position at the reference aperture 82.

To facilitate proper location of the sample holder 80, pins 156 extend outwardly from the bottom of the holder to engage in corresponding slots in the carriage 125 to accurately position the sample holder with respect to the carriage.

Figure 7:
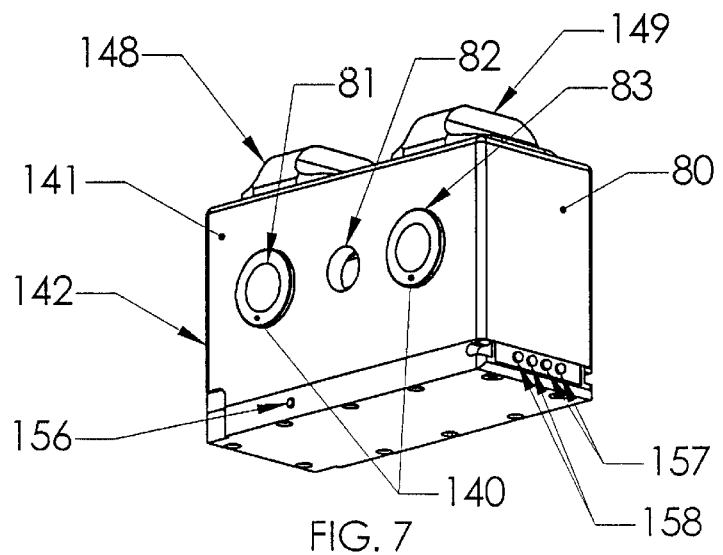
FIG. 7 is a perspective view of a preferred sample holder for transmission measurements in accordance with the invention.
Figure 8:
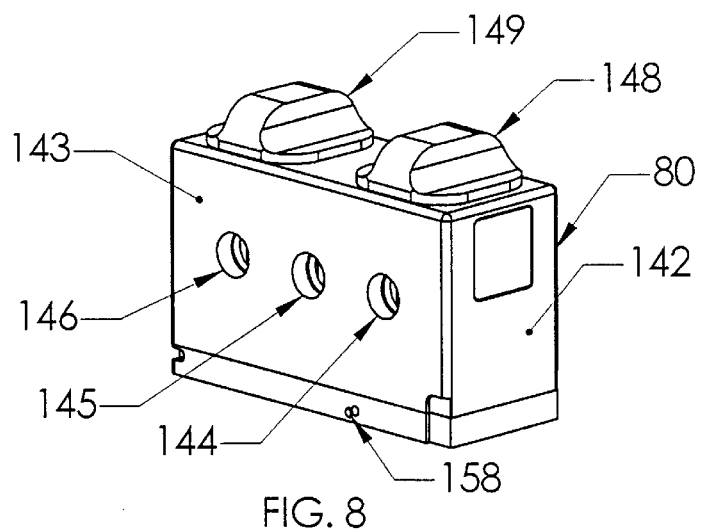
FIG. 8 is a perspective view of the sample holder of FIG. 7 shown generally from the back side of the sample holder.
Figure 9:
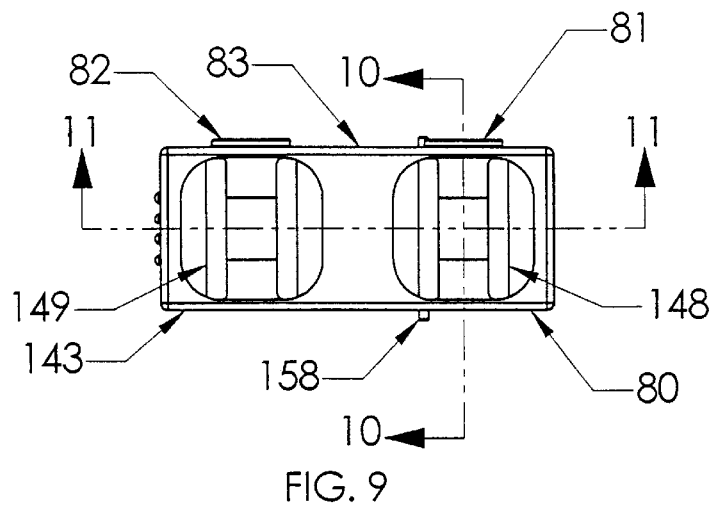
FIG. 9 is a top plan view of the sample holder of FIG. 7.
Figure 10:
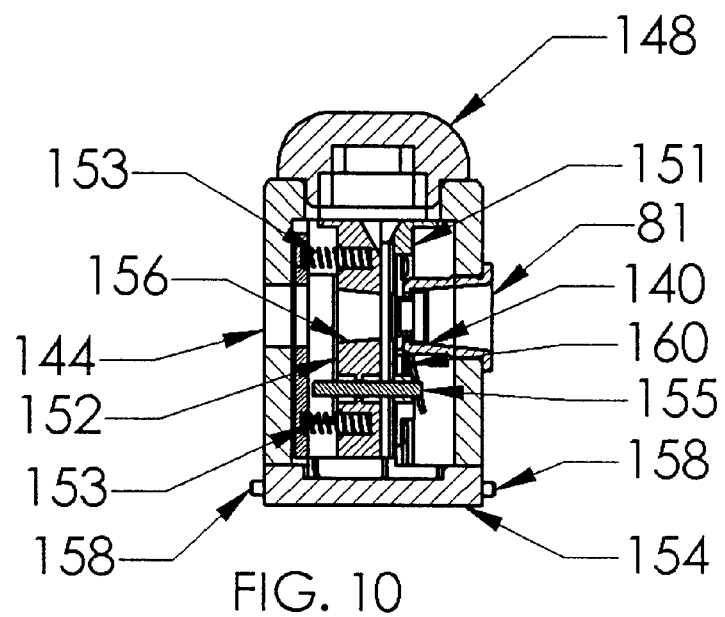
FIG. 10 is a cross-sectional view of the sample holder taken generally along the lines 10—10 of FIG. 9.
Figure 11:
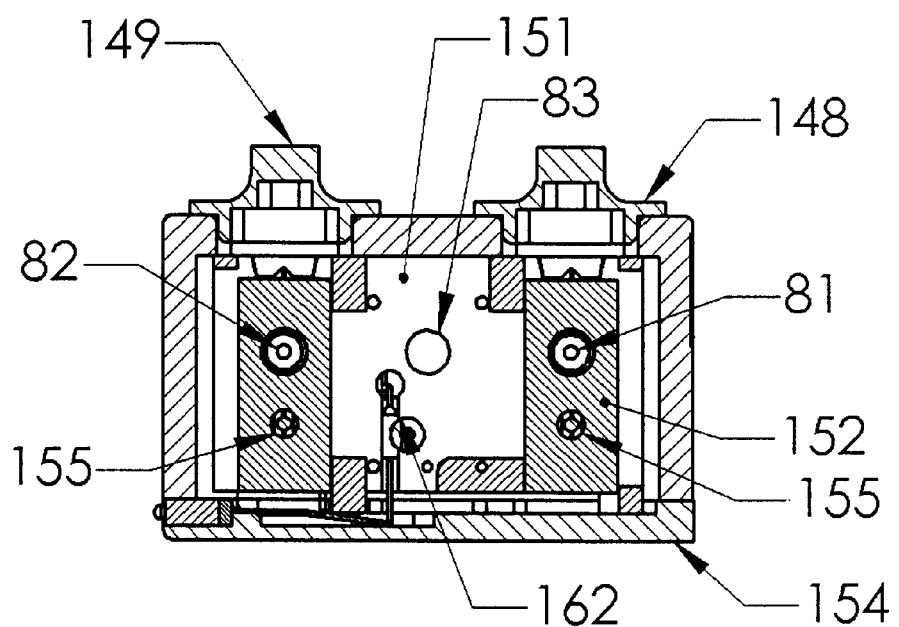
FIG. 11 is a cross-sectional view of the sample holder taken generally along the lines 11—11 of FIG. 9.

The sample holder may be heated to control the temperature of the sample and the reference material. As illustrated in FIG. 7, the sample holder includes electrical contact power input plugs 157 and electrical signal contact plugs 158. The plugs 157 are connected to wiring which extends to electrical heater elements 160 mounted to the front plate 151. The temperature of the plate is monitored by a sensor (e.g., a thermocouple) 162 which is connected to the electrical contacts 158. The controller for the system thus receives a signal indicative of the temperature of the plate 151, and thus of the sample and the reference, and can supply power to the electrical heater plugs 157 as needed to maintain a controlled temperature in the sample compartment and the reference compartment.

The structure of the integrating sphere 92 is shown in more detail with reference to FIGS. 12–14. The integrating sphere 92 may be formed of two sections 170 and 171 each formed of a block of metal (e.g., aluminum) with mating hemispherical depressions formed in them to define a spherical cavity 173 when the two half sections 170 and 171 are assembled together. The surfaces 174 of the spherical space 173 are preferably formed with a diffuse reflecting finish and are preferably gold plated for maximum reflectability and resistance to tarnish. As best shown in FIG. 13, a flip panel 176 is mounted about a pivot 177 to the top section 171 and is operated by action of a solenoid 179 to flip between a first position, as shown in FIG. 13, covering the outlet opening 93 to a second position in which an opening 180 in the flip panel 176 aligns with the outlet opening 93 to allow the illuminating light to pass therethrough. The solenoid 179 is connected to the system controller which controls the position of the flip panel 176. When the flip panel 176 is in its position shown in FIG. 13, blocking the outlet opening 93, the illuminating light that passes through the inlet opening 91 will be blocked by and reflected from the flip panel 176 and diffusely reflected through the interior of the integrating sphere and detected by the detector 98. The flip panel 176 is preferably also formed with a diffuse reflecting surface and may be gold plated for good reflection and tarnish resistance properties. By carrying out tests with the flip panel 176 in its position blocking the outlet opening, calibration measurements can be taken from the signal from the detector 98 to determine the baseline signal at maximum reflection and without a sample. When a test is to be made on a sample, the flip panel 176 may be flipped by the solenoid 179 to its second position in which the opening 180 aligns with the output opening 93, allowing illuminating light to reach a sample mounted in proper position above the outlet opening.

As illustrated in the cross-sectional view of FIG. 14, the shield 96 may comprise a resilient pad, e.g., formed of a rubber or other elastomer, which fits within an (e.g., circular) opening 185 in a frame 186. The circular or washer shaped pad 96 shown in FIG. 14 has a central opening 188 which is positioned to fit over the outlet opening 93 so that the illuminating light can pass up through the outlet opening 93 (when the flip panel 176 is moved to its position wherein the opening 180 is aligned with the outlet opening 93). The opening 188 in the shield 96 is sized and shaped to engage with the periphery of a tablet of a particular size and shape. For example, as shown in FIG. 15, the opening 188 may have a circular shape which is shaped to match the outer side periphery of a round tablet 190 as shown for illustration in FIG. 15. For convenience, the various forms of pharmaceuticals (e.g., tablets, capsules, caplets, pills, etc.) will be simply referred to herein as a "tablet." The shape and size of the opening 188 is adapted to closely match the outer periphery of the tablet 190 so that when the operator presses the tablet 190 into the opening 188, the resilient material of the shield formed of the pad 184 engages firmly and resiliently with the sidewalls of the tablet 190 to substantially block off the passage of any light around the tablet 190. Preferably, the material of the pad 184 forming the shield is essentially opaque to the illuminating infrared radiation, substantially blocking the passage of any infrared light therethrough and with preferably very little or no reflection of infrared light from the pad itself. A separate pad 184 would be utilized for each different size and shape of pharmaceutical tablet so that the shape and size of the opening 188 would again closely match the lateral periphery of the tablet both in size and shape, pressing slightly against the lateral edges of the tablet without blocking light from reaching the tablet over its entire bottom surface to allow the maximum passage of light from the beam 90 to and through the tablet without interference from the shield 96. As also illustrated in FIG. 14, a thin transparent window 191 extends over the flip panel 76 to support a tablet on its surface. The material of the window 191 is preferably selected from a material that is both transmissive of infrared light and relatively durable and scratch resistant.

Figure 5:
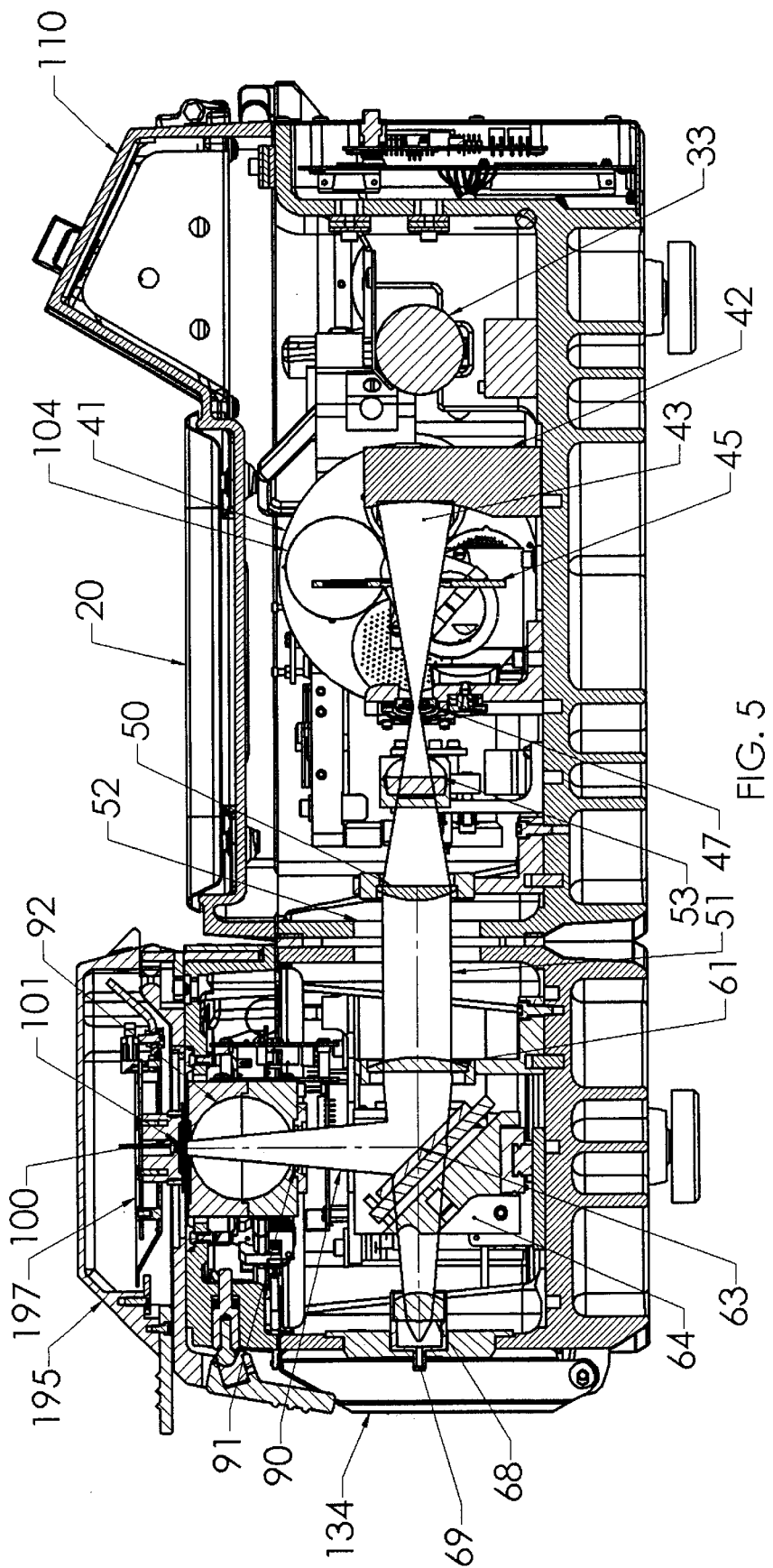
FIG. 5 is a more detailed cross-sectional view of the spectrometer system of the invention taken generally along the lines 5—5 of FIG. 4.

As shown with reference to FIG. 5, a cover 195 that is hingedly mounted to the sampling compartment enclosure 60 carries the detector 100 mounted within a block 197 which may be formed of a resilient material, e.g., rubber or an elastomer plastic. After a tablet has been inserted in the opening 188 in the shield, the cover 195 can be closed to bring the block 197 down into close proximity and preferably engagement with the surface of the shield in the area surrounding the opening 188 where the tablet is held. The closing of the cover also brings the detector 100 into close proximity to the tablet so that light transmitted through the tablet will impinge on the detector and substantially no ambient light will reach the detector.

As noted above, the shield 96 functions to engage the lateral edges of a tablet to substantially block the illuminating light from passing around the tablet while allowing essentially all of the tablet to be exposed to the illuminating light. Many tablets have a circular outer periphery. Where such tablets are to be analyzed, a shield in accordance with the invention may be used as illustrated in FIGS. 16–20. The shield 96 of FIG. 16 is formed to provide an adjustable iris which can engage the lateral side edges of a circular tablet of any size. The adjustable iris shield is referenced generally at 200 in FIGS. 16–20. The iris shield 200 includes an outer base ring 201 which is formed to be mounted to the support panel 186 in the opening 185, a rotatable iris ring 202, a support ring 203 within which the iris ring 202 is mounted for rotation relative to the support ring 203, and an elevational adjustment ring 205 to which the support ring 203 is mounted. Threads 206 on the outside periphery of the elevational adjustment ring 205 engage with threads 207 on the inside periphery of the base ring 207. The iris ring 202 may be a commercial iris of the type used to provide an adjustable aperture, e.g., Edmund Scientific D41,973, 1.2–41 mm iris aperture. The assembly comprised of the iris ring 202 mounted within the support ring 203 on the adjustable ring 205 is then mounted to the base ring 201. Rotation of the iris ring 202 by an operator relative to the support ring 203 (and the elevation ring 205) narrows or widens (depending on the direction of rotation of the ring 202) the circular periphery of a central opening in iris plates carried on the ring 202, which function in the same manner as the adjustable iris of a camera. The iris plates are relatively thin compared to the thickness of the pill or tablet and will engage the outermost edge of the periphery of the circular tablet. The elevational adjustment ring 205 can be used by the operator to raise or lower the position of the iris ring 202, depending on the direction in which the elevational ring 205 is rotated by the user relative to the base ring 201, to bring the iris ring plates to the level of the outer periphery of the tablet above the surface of the window 191. The user rotates the iris ring until the iris plates will engage the outermost periphery of the circular tablet, allowing the tablet to remain in contact with the window 191 while nonetheless substantially blocking passage of any illuminating light past the tablet. Again, engagement by the blocking iris, which thus shields the exterior of the tablet from passage of illuminating light past the tablet, nonetheless allows the entire surface of the tablet to be illuminated with the infrared light.

Figure 20:
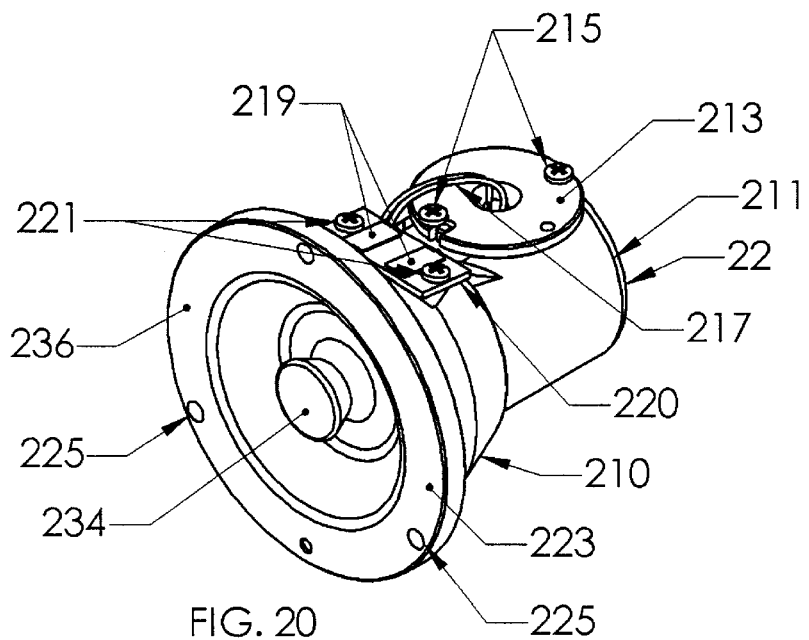
FIG. 20 is a perspective view of an exemplary replaceable infrared source in accordance with the present invention.
Figure 21:
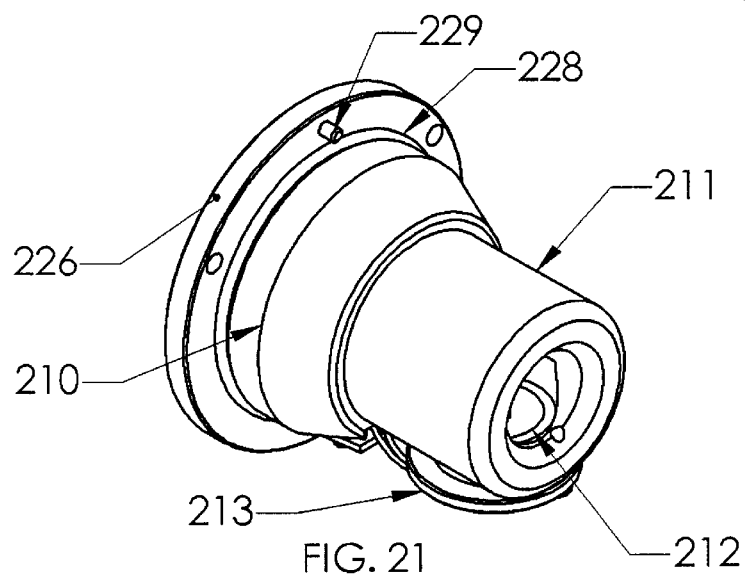
FIG. 21 is another perspective view of the infrared source of FIG. 20.
Figure 22:
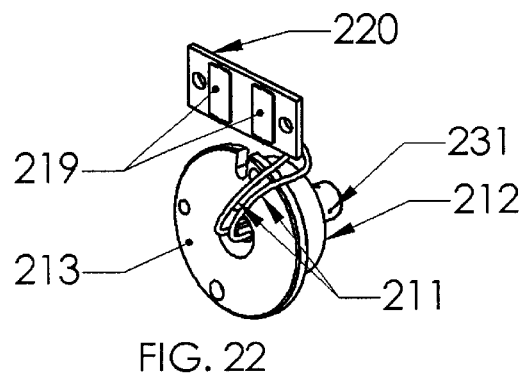
FIG. 22 is a perspective view of a replaceable source element that may be used in the source of FIG. 20.
Figure 23:
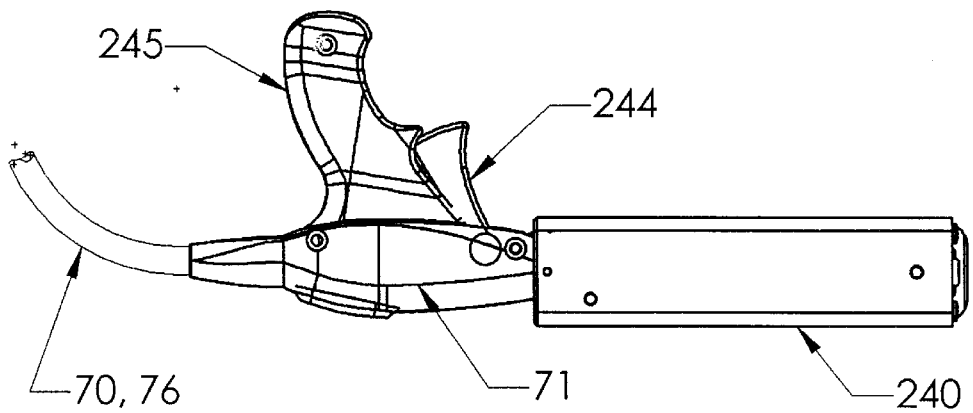
FIG. 23 is a side view of a cradle unit in accordance with the present invention with a fiber optic probe inserted therein for holding the probe when it is not in use and for optionally taking calibration measurements on the probe.
Figure 24:
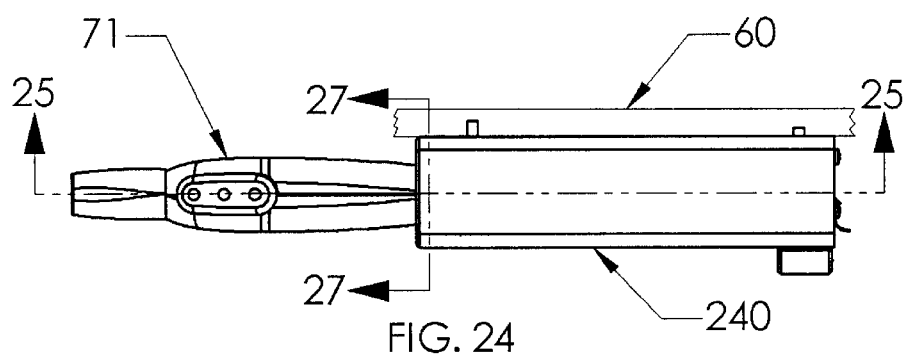
FIG. 24 is a top view of the cradle unit with the probe therein as in FIG. 23.

A more detailed view of the construction of a preferred infrared source 22 is shown in FIGS. 20–22. The source 22 is adapted to be removably mounted within the enclosure 21 so that the infrared source can be readily replaced by an operator when necessary without requiring realignment of the system. To ensure that the system remains aligned and calibrated, the actual source filament must be precisely located with respect to the optical elements in the main beam path. As shown in the figures, the source 22 includes a main housing 210 having a source enclosure 211 to which a replaceable source 212 (e.g., an infrared light source available commercially from Sylvania-Osram) is mounted. The source 212 includes a mounting plate 213 which is secured to the enclosure 211 by screws 215. Lead wires 217 extend from the source to contact pads 219 on a small circuit board 220 which is secured to the main housing by screws 221. When the source 22 is inserted into its position within the enclosure 21, the contact pads 219 are engaged with electrical supply contacts (not shown) in the enclosure to supply electrical power thereto under the control of the system controller. The housing 210 is secured to the enclosure 21 by engagement of screws (not shown) through openings 225 in a flange 226 on the front of the housing 210. The back face 228 of the flange 226 is machined flat and is adapted to engage against a flat surface of the enclosure 21 to precisely orient the housing 210, and the source filament carried in it, in one dimension while the other two dimensions are controlled by a shaft 230 concentrically fixturing into a bore in the housing 21. A pin 229 extending from the back face 228 of the flange fits into a corresponding slot (not shown) in the enclosure 21 to precisely define the rotational position of the source filament. A source which has burned out or is otherwise in need of replacement can be replaced by unscrewing the screws 215 and 221 to remove the filament unit 212 which, as best illustrated in FIG. 22, includes the base plate 213 with the filament 231 mounted to it. When the filament unit 212 is inserted back into its position in the housing and is secured in place with the screws 215, the filament 231 itself is precisely located with respect to the housing 210, and when the operator secures the housing to the enclosure 21 by mounting the source 22 in place and securing it with screws threaded through the openings 225, precise location of the filament 231 with respect to the optical elements of the system is obtained. For convenience, as shown in FIG. 20, a handle or knob 234 may be formed on the exterior portion of the housing 210 to facilitate insertion and removal of the source 22 as a unit.

Figure 25:
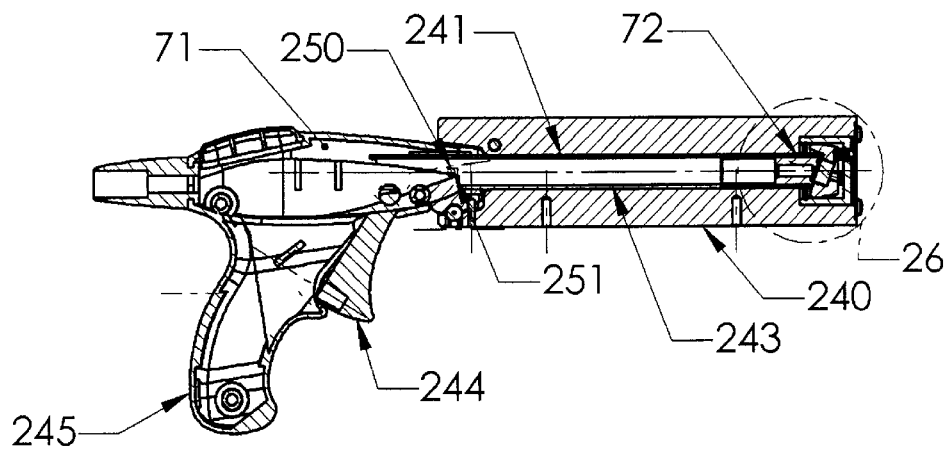
FIG. 25 is a cross-sectional view of the probe and cradle unit taken generally along the lines 25—25 of FIG. 24.
Figure 26:
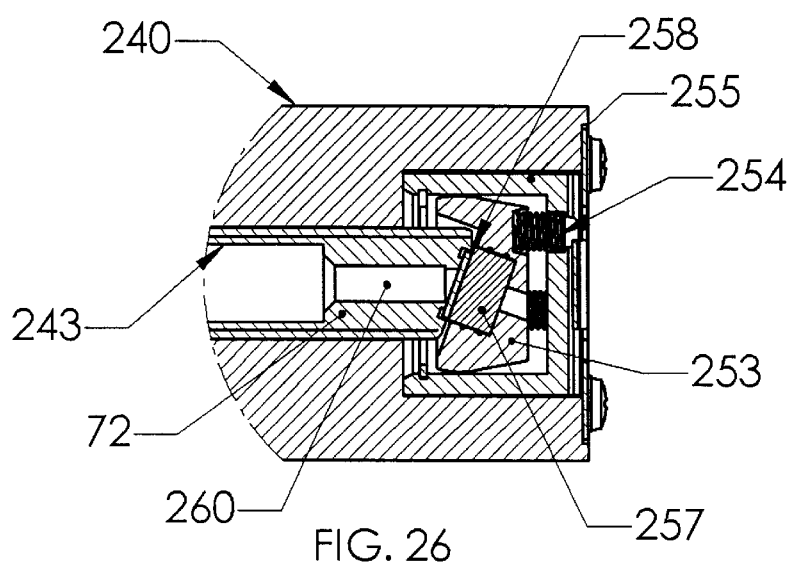
FIG. 26 is a more detailed cross-sectional view of the distal end of the cradle unit and the probe tip held therein.
Figure 27:
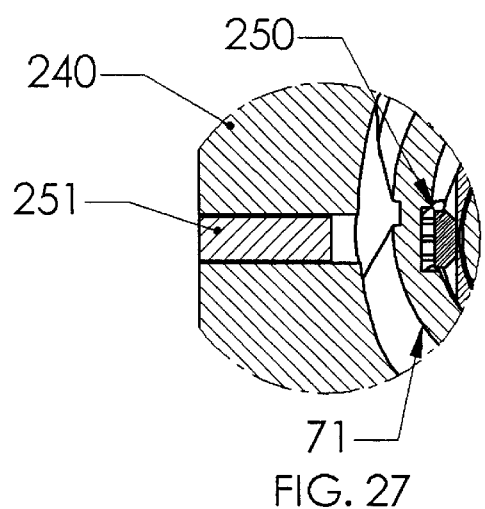
FIG. 27 is a partial cross-sectional view of the probe and cradle unit showing the Hall effect proximity sensor and an activating magnet.

As discussed above, the spectrometer system of the present invention may utilize a probe 71 for analysis of materials at a position remote from the sampling compartment of the spectrometer. It is also desirable that the probe 71 be periodically calibrated for accuracy of measurements made by the probe. To facilitate this calibration and to provide a convenient storage position for the probe, as illustrated in FIGS. 23–26 a cradle unit 240 may be mounted to the enclosure 60 for the sample compartment which has an open socket 241 (as shown in the cross-sectional view of FIG. 25) which is sized and shaped to fit an elongated tube portion 243 of the probe 71. The sensing tip 72 of the probe is mounted at the end of the tube 243. The probe 71 may be of conventional construction, including a trigger switch 244 mounted on a handle grip 245 which allows the operator to selectively turn on the system to provide the illuminating infrared radiation to the probe tip 72 and to collect the reflected light from the sample at the probe tip. The probe preferably includes a proximity sensor 250 (e.g., a magnetic Hall effect switch) which is activated by a magnet 251 when the probe tip 72 is sufficiently close to the end of the cradle, as illustrated in FIG. 25 and the more detailed cross-sectional view of FIG. 27. The sensor 250 is electrically connected to the controller for the system, allowing the controller to determine when the probe 71 has been inserted into the cradle unit 240 and the probe tip 72 is in position at the end of the cradle. As best illustrated in the detailed cross-sectional view of the end of the cradle shown in FIG. 26, at the end of the cradle unit 240 is mounted a stop member 253 which is mounted by springs 254 in a retainer cup 255 which itself is secured in a blind hole formed in the end of the housing of the cradle unit 240. The stop member 253 has an infrared reflective member 257 mounted therein which is positioned to engage against the end face 258 of the probe tip and to cover the outlet and inlet ends of the optical fibers 70 and 76 (not shown in FIG. 26) which are held within a bore 260 in the probe tip 72. The material of the member 257 is preferably selected to prove efficient diffuse reflection of infrared light back to the probe tip, and may be formed of a commercially available material such as Spectralon™, available from Labsphere.

When the probe 71 is not being used for measurements of a sample, the operator inserts the probe tube 243 into the socket 241 until the probe tip 72 reaches and engages the stop 253. At this point, the probe is securely held within the cradle 240. The proximity sensor 250 provides an output signal to the system controller indicating that the probe tip is at the position engaging the stop member 253 so that the ends of the optical fiber cables 70 and 76 are adjacent to the reflecting element 258. At this time, the system controller may carry out calibration of the probe by providing infrared light on the first branch beam path to the probe on the supply optical fiber cable 70, with this light being reflected substantially completely from the reflecting element 258 back into the inlet end of the return optical fiber cable 76 and thence to the detector 77. In this manner, the controller can determine the baseline spectral response of the probe 71 using the attenuator filters and the reference material disc in the filter wheel 41 as discussed above.

Figure 28:
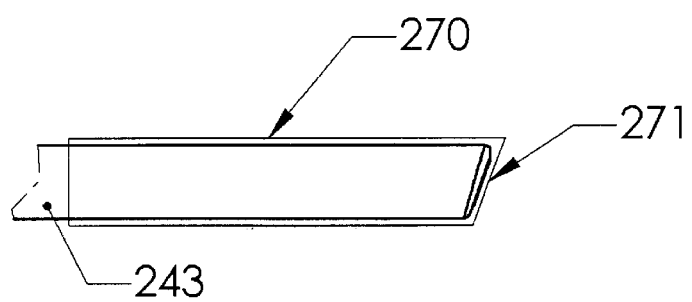
FIG. 28 is a side view of the probe tube having a protective sheath thereon.

As illustrated in FIG. 28, a plastic sheath 270 may be slipped over the probe tube 243 to protect the probe tube and the probe tip from contamination by a sample into which the probe is inserted. The sheath 270 may be formed so that it can be disposed of after each measurement and replaced before the next measurement. The sheath 270 has an end panel 271 at the tip which is formed to be essentially transparent to the infrared wavelengths used. The sheath may be formed of plastics such as polyethylene or polypropylene.

It is understood that the invention is not confined to the particular embodiments set forth herein as illustrative, but embraces all such modified forms thereof as come within the scope of the following claims.

What is claimed is:

1. A multifunctional infrared spectrometer system comprising:
   (a) a source of infrared radiation which provides a beam of infrared;
   (b) an interferometer which receives the beam from the source and produces a modulated output beam;
   (c) at least two spatially separated infrared detectors;
   (d) optical elements transmitting the modulated output beam from the interferometer on a main beam path to a junction position;
   (e) optical elements defining a first branch beam path from the junction position to a first sample position and then to a first of the detectors, and optical elements defining a second branch beam path from the junction position to a second sample position and then to a second of the detectors;
   (f) a multi-position mirror element movable between at least two positions, wherein in a first position of the mirror element the beam on the main beam path is passed on the first branch beam path to the first sample position an thence to the first detector and wherein in the second position of the mirror element the main beam is passed on the second branch beam path to the second sample position and thence to the second detector; and
   (g) further including a third infrared detector spatially separated from the other infrared detectors, and optical elements defining a third branch beam path from the junction position to a third sample position and thence to the third detector, and wherein the multi-position mirror element is movable to a third position in which the mirror element passes the main beam on the third branch beam path to the third sample position and thence to the third detector.

2. The spectrometer system of claim 1 wherein the multi-position mirror element comprises a first deflecting mirror having a deflecting mirror surface in a plane oriented at an acute angle with respect to the axis of the main beam path at the junction position and a second deflecting mirror disposed laterally of the first deflecting mirror and having a mirror surface in a plane oriented at an acute angle to the axis of the main beam path, the plane of the surface of the second deflecting mirror non-parallel to the plane of the surface of the first deflecting mirror, wherein the deflecting mirrors are mounted for lateral translation on a carriage between three lateral positions of the mirror element, such that in one of the positions both of the deflecting mirrors are out of the main beam path and the main beam passes the mirrors undeflected onto one of the branch beam paths, wherein a second laterally moved position the first deflecting mirror intercepts the main beam to deflect it onto another of the branch beam paths, and wherein in the third lateral position the second deflecting mirror intercepts the main beam and deflects the beam onto another branch beam path.

3. The spectometer system of claim 1 wherein the optical elements defining the main beam path include a focussing lens that provides a converging beam to the junction position.

4. The spectrometer system of claim 1 wherein the optical elements defining the main beam path include a focussing lens that provides a converging beam to the junction position, and including a sample holder mounted in one of the branch beam paths, the sample holder having a sample port therein at which a sample to be tested may be held for transmission of infrared light therethrough, the infrared light passed through the sample at the sample port directed by optical elements to one of the infrared detectors.

5. The spectrometer system of claim 1 wherein the main beam path includes a focussing mirror receiving the beam from the interferometer and converging the beam to a focal position from which the beam diverges, and further including an aperture element having an aperture at the focal position to spatially define the beam, the aperture element positioned to block stray light passing back in the beam path to the interferometer.

6. A multifunctional infrared spectrometer system comprising:
   (a) a source of infrared radiation which provides a beam of infrared;
   (b) an interferometer which receives the beam from the source and produces a modulated output beam;
   (c) at least two spatially separated infrared detectors;
   (d) optical elements transmitting the modulated output beam from the interferometer on a main beam path to a junction position;
   (e) optical elements defining a first branch beam path from the junction position to a first sample position and then to a first of the detectors, and optical elements defining a second branch beam path from the junction position to a second sample position and then to a second of the detectors;
   (f) a multi-position mirror element movable between at least two positions, wherein in a first position of the mirror element the beam on the main beam path is passed on the first branch beam path to the first sample position and thence to the first detector and wherein in the second position of the mirror element the main beam is passed on the second branch beam path to the second sample position and thence to the second detector;
   (g) wherein the optical elements defining the main beam path include a focussing lens that provides a converging beam to the junction position; and
   (h) wherein the output beam from the interferometer is collimated and wherein the optical elements in the main beam path further include a focussing mirror mounted to intercept the collimated output beam of the interferometer and converge the beam to a focal position, an aperture member at the focal position having an aperture selected to spatially define the beam at the focal position and to block stray light from passing back along the main beam path to the interferometer, wherein the beam passed through the aperture diverges and is intercepted by a collimating lens that provides a collimated beam to the focussing lens that provides a converging beam to the junction position.

7. The spectrometer system of claim 6 further including at least one indexable filter wheel mounted to intercept the output beam from the interferometer on the main beam path and having multiple attenuator element therein, the filter wheel indexable between plural positions to selectively insert attenuators in the main beam path to provide selected attenuation of the beam in the main beam path and including at least one position at which the beam passes unimpeded through the filter wheel.

8. The spectrometer system of claim 7 further including a second indexable filter wheel mounted in the main beam path to intercept the converging beam ahead of the aperture, the second filter wheel having a plurality of filter elements therein and indexable between positions at which selected filter elements are interposed in the converging beam path to provide selected attenuation of the converging beam, an including at least one position in which the converging beam passes unimpeded through the filter wheel.

9. The spectrometer system of claim 7 wherein at least one of the attenuator elements in the filter wheel comprises a polystyrene wavelength accuracy reference disc.

10. The spectrometer system of claim 6 further including a deflecting mirror mounted for lateral movement from a first position in which it is adjacent to but out of the diverging beam passed through the aperture to a second position in which the deflecting mirror intercepts the diverging beam from the aperture and deflects the beam to a lens which provides a collimated output beam that may be directed to other optical components.

11. A multifunctional infrared spectrometer system comprising:
   (a) a source of infrared radiation which provides a beam of infrared;
   (b) an interferometer which receives the beam from the source and produces a modulated output beam;
   (c) at least two spatially separated infrared detectors;
   (d) optical elements transmitting the modulated output beam from the interferometer on a main beam path to a junction position;
   (e) optical elements defining a first branch beam path from the junction position to a first sample position and then to a first of the detectors, and optical elements defining a second branch beam path from the junction position to a second sample position and then to a second of the detectors;
   (f) a multi-position mirror element movable between at least two positions, wherein in a first position of the mirror element the beam on the main beam path is passed on the first branch beam path to the first sample position an thence to the first detector and wherein in the second position of the mirror element the main beam is passed on the second branch beam path to the second sample position and thence to the second detector;
   (g) wherein the optical elements defining the main beam path include a focussing lens that provides a converging beam to the junction position, and including a sample holder mounted in one of the branch beam paths, the sample holder having a sample port therein at which a sample to be tested may be held for transmission of infrared light therethrough, the infrared light passed through the sample at the sample port directed by optical elements to one of the infrared detectors; and
   (h) wherein the sample holder comprises a sample body having in addition to the sample port and spaced laterally therefrom an open pass-through port and a reference port, the sample holder body having a sample receptacle to receive a sample to be tested in position to have infrared light passed therethrough at the sample port and a reference receptacle to hold a reference material to have infrared light passed therethrough at the reference port, and an indexable carriage on which the sample holder may be mounted, and means for driving the carriage with the sample holder mounted thereto between a position in which the sample port is in the branch beam path to a position in which the open port is in the branch beam path to a position in which the reference port is in the branch beam path.

12. The spectrometer system of claim 11 wherein the sample holder has an electrical heating element mounted in the sample body which heats the sample body and a sample held therein when electrical power is supplied thereto and an electrical temperature sensing element mounted in the sample body for monitoring the temperature of the sample body, whereby the temperature of the sample body may be sensed and the heating of the sample body controlled to maintain a desired temperature.

13. The spectrometer system of claim 11 wherein circular aperture elements are mounted at the sample port, the reference port, and the pass-through port of the sample holder to define spatially limited apertures for the infrared beam passed through the ports.

14. A multifunctional infrared spectrometer system comprising:
   (a) a source of infrared radiation which provides a beam of infrared;
   (b) an interferometer which receives the beam from the source and produces a modulated output beam;
   (c) at least two spatially separated infrared detectors;
   (d) optical elements transmitting the modulated output beam from the interferometer on a main beam path to a junction position;
   (e) optical elements defining a first branch beam path from the junction position to a first sample position and then to a first of the detectors, and optical elements defining a second branch beam path from the junction position to a second sample position and then to a second of the detectors;
   (f) a multi-position mirror element movable between at least two positions, wherein in a first position of the mirror element the beam on the main beam path is passed on the first branch beam path to the first sample position and thence to the first detector and wherein in the second position of the mirror element the main beam is passed on the second branch beam path to the second sample position and thence to the second detector; and
   (g) wherein the optical elements in one of the branch beam paths include an optical fiber supply cable leading to a probe, a focussing lens for focussing a beam in the branch beam path into the optical fiber supply cable, the probe having a probe tip at which the supply cable terminates at an outlet end at which infrared is projected, and an optical fiber return cable having an inlet end at the probe tip adjacent to the outlet end of the optical fiber supply cable and which extends to one of the infrared detectors and transmits infrared radiation that has been reflected from a sample and received at the inlet end of the return cable to the infrared detector.

15. The spectrometer system of claim 14 wherein the probe includes an elongated tubular portion at one end of which is mounted the probe tip, and a cradle unit having an open socket which is sized and shaped to fit the elongated tube portion such that the tube portion may be inserted into the open socket, the cradle unit including a stop member closing the open socket against which the probe tip is engaged when the tubular portion is inserted fully into the open socket, the stop member including an infrared reflective member which provides diffuse reflection of infrared incident thereon from the optical fiber cable to reflect it to the optical fiber return cable when the probe tip is engaged against the stop member, and a sensor mounted to the cradle unit that provides an output signal when the probe tip is adjacent to the stop member, whereby when the probe is not being used for testing a sample it can be inserted into the receptacle of the cradle wherein calibration tests may be carried out on the probe by providing infrared to the branch beam path leading to the optical fiber supply cable that is reflected off of the reflective member into the optical fiber return cable and thence to the infrared detector.

16. A multifunctional infrared spectrometer system comprising:
(a) a source of infrared radiation which provides a beam of infrared;
(b) an interferometer which receives the beam from the source and produces a modulated output beam;
(c) at least two spatially separated infrared detectors;
(d) optical elements transmitting the modulated output beam from the interferometer on a main beam path to a junction position;
(e) optical elements defining a first branch beam path from the junction position to a first sample position and then to a first of the detectors, and optical elements defining a second branch beam path from the junction position to a second sample position and then to a second of the detectors;
(f) a multi-position mirror element movable between at least two positions, wherein in a first position of the mirror element the beam on the main beam path is passed on the first branch beam path to the first sample position and thence to the first detector and wherein in the second position of the mirror element the main beam is passed on the second branch beam path to the second sample position and thence to the second detector; and
(g) wherein one of the branch beam paths receives a converging infrared beam from the main beam path and wherein the optical elements in that branch beam path include an integrating sphere having a hollow spherical interior, an inlet opening in the integrating sphere which receives the converging beam, an outlet opening in the integrating sphere through which the converging beam passes, a window over the outlet opening on which a sample such as a tablet may be placed in a sample position, and a detector mounted to the integrating sphere to receive infrared radiation reflected from the interior surfaces of the integrating sphere, the interior surfaces of the integrating sphere formed to provide diffuse reflection, whereby infrared reflected from a sample held on the window in a sample position will be diffusely reflected in the integrating sphere to the infrared detector mounted to the integrating sphere.

17. The spectrometer system of claim 16 wherein another infrared detector is mounted adjacent to the sample position above the window to receive infrared radiation passed through the outlet opening of the integrating sphere, the window, and a sample held in the sample position, to detect infrared transmitted through the sample.

18. The spectrometer system of claim 17 further including a shield mounted at the sample position between the integrating sphere and the detector that detects the infrared transmitted through the outlet opening of the integrated sphere and through the sample, the shield having an inner periphery conforming to the outer periphery of a tablet to be supported on the window above the integrating sphere, the shield blocking infrared radiation, thereby substantially blocking infrared radiation from passing around the lateral periphery of a tablet held at the sample position above the outlet opening of the integrating sphere.

19. The spectrometer system of claim 18 wherein the shield comprises an elastomer pad having an interior opening therein with an inner periphery sized to conform to the outer periphery of the tablet to be held to resiliently engage the outer periphery of the tablet to block off infrared radiation from passing around the tablet.

20. The spectrometer system of claim 18 wherein the shield comprises an adjustable iris, the diameter of the inner periphery of which can be adjusted by an operator to engage the outer periphery of a circular tablet held at the sample position and supported on the window above the outlet opening of the integrating sphere, the adjustable iris when engaged with a tablet blocking infrared radiation from passing around the periphery of the tablet to the infrared detector mounted to receive infrared radiation transmitted through the tablet.

21. The spectrometer system of claim 20 including an elevational adjustment ring to which the adjustable iris is mounted, the elevational adjustment ring operable by an operator to adjust the height of the inner periphery of the iris above the window to engage against the outer periphery of a tablet.

22. The spectrometer system of claim 18 further including a flip panel mounted between the outlet opening of the integrating sphere and the window on which the sample is supported above the outlet opening, the flip panel movable between a position in which the flip panel allows infrared radiation to pass from the outlet opening through the window to a sample held on the window to a position in which the flip panel blocks the infrared radiation from passing through the window to the sample, the surface of the flip panel facing the outlet opening of the integrating sphere having an infrared reflective surface such that when the flip panel blocks the outlet opening infrared radiation incident thereon will be reflected into the integrating sphere and be detected by the detector mounted in the integrating sphere to allow calibration of the infrared beam provided on the branch beam path to the integrating sphere.

23. A multifunctional infrared spectrometer system comprising:
(a) a source of infrared radiation which provides a beam of infrared;
(b) an interferometer which receives the beam from the source and produces a modulated output beam;
(c) at least two spatially separated infrared detectors;
(d) optical elements transmitting the modulated output beam from the interferometer on a main beam path to a junction position;
(e) optical elements defining a first branch beam path from the junction position to a first sample position and then to a first of the detectors, and optical elements defining a second branch beam path from the junction position to a second sample position and then to a second of the detectors;
(f) a multi-position mirror element movable between at least two positions, wherein in a first position of the mirror element the beam on the main beam path is passed on the first branch beam path to the first sample position and thence to the first detector and wherein in the second position of the mirror element the main beam is passed on the second branch beam path to the second sample position and thence to the second detector; and (h) wherein the source comprises a source housing having a source enclosure to which an infrared source element is mounted, the source housing having an outwardly extending flange with an inner surface defining a plane which can be engaged against a surface of a spectrometer enclosure to define a position of the housing.

24. The spectrometer system of claim 23 wherein the source element is located at a known position in the source enclosure when the source element is secured to the source enclosure, and including electrical contact pads electrically connected to the source element that are mounted on the source housing in a position to be engaged with electrical contacts on a spectrometer enclosure thereby to make electrical contact to provide power to the source element when the source housing is inserted into the enclosure and secured thereto.

25. A multifunctional infrared spectrometer system comprising:

(a) a source of infrared radiation which provides a beam of infrared;

(b) an interferometer which receive the beam from the source and produces a modulated output beam;

(c) at least three spatially separated infrared detectors;

(d) optical elements transmitting the modulated output beam from the interferometer on a main beam path to a junction position;

(e) optical elements defining a first branch beam path from the junction position to a first sample position and then to a first of the detectors, optical elements defining a second branch beam path from the junction position to a second sample position and then to a second of the detectors, and optical elements defining a third branch beam path from the junction position to a third sample position and thence to the third of the detectors; and (f) a multi-position mirror element movable between three positions, wherein in a first position of the mirror element the beam on the main beam path is passed on the first branch beam path to the first sample position and thence to the first detector, and wherein in the second position of the mirror element the main beam is passed on the second branch beam path to the second sample position and thence to the second detector, and wherein in the third position of the mirror element, the main beam is passed on the third branch beam to the third sample position and thence to the third detector, the multi-position mirror element comprising a first deflecting mirror having a deflecting mirror surface in a plane oriented at an acute angle with respect to the axis of the main beam path at the junction position and a second deflecting mirror disposed laterally of the first deflecting mirror and having a mirror surface in a plane oriented at an acute angle to the axis of the main beam path, the plane of the surface of the second deflecting mirror non-parallel to the plane of the surface of the first deflecting mirror, wherein the deflecting mirrors are mounted for lateral translation on a carriage between three lateral positions of the mirror element, such that in one of the positions both of the deflecting mirrors are out of the main beam path and the main beam passes the mirrors undetected onto one of the branch beam paths, wherein in a second laterally moved position the first deflecting mirror intercepts the main beam to deflect it onto another of the branch beam paths, and wherein in the third lateral position the second deflecting mirror intercepts the main beam and deflects the beam onto another branch beam path.

26. The spectrometer system of claim 25 wherein the optical elements defining the main beam path include a focussing lens that provides a converging beam to the junction position.

27. The spectrometer system of claim 26 wherein the output beam from the interferometer is collimated and wherein the optical elements in the main beam path further include a focussing mirror mounted to intercept the collimated output beam of the interferometer and converge the beam to a focal position, an aperture member at the focal position having an aperture selected to spatially define the beam at the focal position and to block stray light from passing back along the main beam path to the interferometer, wherein the beam passed through the aperture diverges and is intercepted by a collimating lens that provides a collimating beam to the focussing lens that provides a converging beam to the junction position.

28. The spectrometer system of claim 27 further including at least one indexable wheel mounted to intercept the output beam from the interferometer on the main beam path and having multiple attenuator elements therein, the filter wheel indexable between plural positions to selectively insert attenuators in the main beam path to provide selected attenuation of the beam in the main beam path and including at least one position at which the beam passes unimpeded through the filter wheel.

29. The spectrometer system of claim 28 further including a second indexable filter wheel mounted in the main beam path to intercept the converging beam ahead of the aperture, the second filter wheel having a plurality of filter elements therein and indexable between positions at which selected filter elements are interposed in the converging beam path to provide selected attenuation of the converging beam, and including at least one position in which the converging beam passes unimpeded through the filter wheel.

30. The spectrometer system of claim 28 wherein at least one of the attenuator elements in the filter wheel comprises a polystyrene wavelength accuracy reference disc.

31. The spectrometer system of claim 29 further including a deflecting mirror mounted for lateral movement from a first position in which it is adjacent to but out of the diverging beam passed through the aperture to a second position in which the deflecting mirror intercepts the diverging beam from the aperture and deflects the beam to a lens which provides a collimated output beam that may be directed to other optical components.

32. The spectrometer system of claim 25 wherein the optical elements defining the main beam path include a focussing lens that provides a converging beam to the junction position, and including a sample holder mounted in one of the branch beam paths, the sample holder having a sample port therein at which a sample to be tested may be held for transmission of infrared light therethrough, the infrared light passed through the sample at the sample port directed by optical elements to one of the infrared detectors, wherein the sample holder comprises a sample body having in addition to the sample port and spaced laterally therefrom an open pass-through port and a reference port, the sample holder body having a sample receptacle to receive a sample to be tested in position to have infrared light passed therethrough at the sample port and a reference receptacle to hold a reference material to have infrared light passed therethrough at the reference port, and an indexable carriage on which the sample holder may be mounted, and means for driving the carriage with the sample holder mounted thereto between a position in which the sample port is in the branch beam path to a position in which the open port is in the branch beam path to a position in which the reference port is in the branch beam path.

33. The spectrometer system of claim 32 wherein the sample holder has an electrical heating element mounted in the sample body which heats the sample body and a sample held therein when electrical power supplied thereto and an electrical temperature sensing element mounted in the sample body for monitoring the temperature of the sample body, whereby the temperature of the sample body may be sensed and the heating of the sample body controlled to maintain a desired temperature.

34. The spectrometer system of claim 32 wherein the circular aperture elements are mounted at the sample port, the reference port, and the pass-through port of the sample holder to define a spatially limited aperture for the infrared beam passed through the ports.

35. The spectrometer system of claim 25 wherein the optical elements in one of the branch beam paths include an optical fiber supply cable leading to a probe, a focussing lens for focussing a beam in the branch beam path into the optical fiber supply cable, the probe having a probe tip at which the supply cable terminates at an outlet end at which infrared is projected, an optical fiber return cable having an inlet end at the probe tip adjacent to the outlet end of the optical fiber supply cable and extending to one of the infrared detectors and that transmits infrared radiation that has been reflected from a sample and received at the inlet end of the return cable to the infrared detector, wherein the probe includes an elongated tubular portion at one end of which is mounted the probe tip, and a cradle unit having an open socket which is sized and shaped to fit the elongated tube portion such that the tube portion may be inserted into the open socket, the cradle unit including a stop member closing the open socket against which the probe tip is engaged when the tubular portion is inserted fully into the open socket, the stop member including an infrared reflective member which provides diffuse reflection of infrared incident thereon from the optical fiber cable to reflect it to the optical fiber return cable when the probe tip is engaged against the stop member, and a sensor mounted to the cradle unit that provides an output signal when the probe tip is adjacent to the stop member, whereby when the probe is not being used for testing a sample it can be inserted into the receptacle of the cradle wherein calibration tests may be carried out on the probe by providing infrared to the branch beam path leading to the optical fiber supply cable that is reflected off of the reflective member into the optical fiber return cable and thence to the infrared detector.

36. The spectrometer system of claim 25 wherein one of the branch beam paths receives a converging infrared beam from the main beam path and wherein the optical elements in that branch beam path include an integrating sphere having a hollow spherical interior, an inlet opening in the integrating sphere which receives the converging beam, an outlet opening in the integrating sphere through which the converging beam passes, a window over the outlet opening on which a sample such as a tablet may be placed in a sample position, and a detector mounted to the integrating sphere to receive infrared radiation reflected from the interior surfaces of the integrating sphere, the interior surfaces of the integrating sphere formed to provide diffuse reflection, whereby infrared reflected from a sample held on the window in a sample position will be diffusely reflected in the integrating sphere to the infrared detector mounted to the integrating sphere.

37. The spectrometer system of claim 36 wherein another infrared detector is mounted adjacent to the sample position above the window to receive infrared radiation passed though the outlet opening of the integrating sphere, the window, and a sample held in the sample position, to detect infrared transmitted though the sample.

38. The spectrometer system of claim 37 further including a shield mounted at the sample position between the integrating sphere and the detector that detects the infrared transmitted through the outlet opening of the integrated sphere and though the sample, the shield having an inner periphery conforming to the outer periphery of a tablet to be supported on the window above the integrating sphere, the shield blocking infrared radiation, thereby substantially blocking infrared radiation from passing around the lateral periphery of a tablet held at the sample position above the outlet opening of the integrating sphere.

39. The spectrometer system of claim 38 wherein the shield comprises an elastomer pad having an interior opening therein with an inner periphery sized to conform to the outer periphery of the tablet to be held to resiliently engage the outer periphery of the tablet to block off infrared radiation from passing around the tablet.

40. The spectrometer system of claim 39 wherein the shield comprises an adjustable iris, the diameter of the inner periphery of which can be adjusted to engage the outer periphery of a circular tablet held at the sample position and supported on the window above the outlet opening of the integrating sphere, the adjustable iris when engaged with a tablet blocking infrared radiation from passing around the periphery of the tablet to the infrared detector mounted to receive infrared radiation transmitted through the tablet, and an elevational adjustment ring to which the adjustable iris is mounted, the elevational adjustment ring operable by an operator to adjust the height of the inner periphery of the iris above the window to engage against the outer periphery of a tablet.

41. The spectrometer system of claim 39 further including a flip panel mounted between the outlet opening of the integrating sphere and the window on which the sample is supported above the outlet opening, the flip panel movable between a position in which the flip panel allows infrared radiation to pass from the outlet opening through the window to a sample held on the window to a position in which the flip panel blocks the infrared radiation from passing through the window to the sample, the surface of the flip panel facing the outlet opening of the integrating sphere having an infrared reflective surface such that when the flip panel blocks the outlet opening infrared radiation incident thereon will be reflected into the integrating sphere and be detected by the detector mounted in the integrating sphere to allow calibration of the infrared beam provided on the branch beam path to the integrating sphere.

42. The spectrometer system of claim 25 wherein the source comprises a source housing having a source enclosure to which an infrared source element is mounted, the source housing having an outwardly extending flange with an inner surface defining a plane which can be engaged against a surface of a spectrometer enclosure to define a position of the housing.

43. The spectrometer system of claim 42 wherein the source element is located at a known position in the source enclosure when the source element is secured to the source enclosure, and including electrical contact pads electrically connected to the source element that are mounted on the source housing in a position to be engaged with electrical contacts on a spectrometer enclosure thereby to make electrical contact to provide power to the source element when the source housing is inserted into the enclosure and secured thereto.

44. The spectrometer system of claim 25 wherein the main beam path includes a focussing mirror receiving the beam from the interferometer and converging the beam to a focal position from which the beam diverges, and further including an aperture element having an aperture at the focal position to spatially define the beam, the aperture element positioned to block stray light passing back in the beam path to the interferometer.

45. An infrared spectrometer system comprising:
   (a) a source of infrared radiation which provides a beam of infrared;
   (b) an interferometer which receives the beam from the source and produces a modulated output beam;
   (c) an infrared detector;
   (d) optical elements transmitting the modulated output beam from the interferometer on a beam path to a sample position and then to the detector, and wherein the optical elements include a focussing lens that provides converging beam to the sample position; and
   (e) a sample holder having a sample port therein at which a sample to be tested may be held in the sample position for transmission of infrared light therethrough, the infrared light passed through the sample at the sample port directed by optical elements to the infrared detector, wherein the sample holder comprises a sample body having in addition to the sample port and spaced laterally therefrom an open pass-through port and a reference port, the sample holder body having a sample receptacle to receive a sample to be tested in position to have infrared light passed therethrough at the sample port an a reference receptacle to hold a reference material to have infrared light passed therethrough at the reference port, and an indexable carriage on which the sample holder may be mounted, and means for driving the carriage with the sample holder mounted thereto between a position in which the sample port is in the beam path at the sample position to a position in which the open port is in the beam path to a position in which the reference port is in the beam path.

46. The spectrometer system of claim 45 wherein the sample holder has an electrical heating element mounted in the sample body which heats the sample body and a sample held therein when electrical power is supplied thereto and an electrical temperature sensing element mounted in the sample body for monitoring the temperature of the sample body, whereby the temperature of the sample body may be sensed and the heating of the sample body electronically controlled to maintain a desired temperature.

47. The spectrometer system of claim 45 wherein circular aperture elements are mounted at the sample port, the reference port, and the pass-through port of the sample holder to define spatially limited apertures for the infrared beam passed through the ports.

48. An infrared spectrometer system comprising:
   (a) a source of infrared radiation which provides a beam of infrared;
   (b) an interferometer which receives the beam from the source and produces a modulated output beam;
   (c) an infrared detector;
   (d) optical elements transmitting the modulated output beam from the interferometer on a beam path including an optical fiber supply cable leading to a probe, a focussing lens for focussing a beam in the beam path into the optical fiber supply cable, the probe having a probe tip at which the supply cable terminates at an outlet end at which infrared is projected, an optical fiber return cable having an inlet end at the probe tip adjacent to the outlet end of the optical fiber supply cable and extending to the infrared detector and that transmits infrared radiation that has been reflected from a sample and received at the inlet end of the return cable to the infrared detector, wherein the probe includes an elongated tubular portion at one end of which is mounted the probe tip; and
   (e) a cradle unit having an open socket which is sized and shaped to fit the elongated tube portion such that the tube portion may be inserted into the open socket, the cradle unit including a stop member closing the open socket against which the probe tip is engaged when the tubular portion is inserted fully into the open socket, the stop member including an infrared reflective member which provides diffuse reflection of infrared incident thereon from the optical fiber cable to reflect it to the optical fiber return cable when the probe tip is engaged against the stop member, and a sensor that provides an output signal when the probe tip is adjacent to the stop member, whereby when the probe is not being used for testing a sample it can be inserted into the receptacle of the cradle wherein calibration test may be carried out on the probe by providing infrared to the beam path leading to the optical fiber supply cable that is reflected off of the reflective member into the optical fiber return cable and thence to the infrared detector.

49. An infrared spectrometer system comprising:
   (a) a source of infrared radiation which provides a beam of infrared;
   (b) an interferometer which receives the beam from the source and produces a modulated output beam;
   (c) optical elements transmitting the modulated output beam from the interferometer on a beam path and providing a converging infrared beam;
   (d) an integrating sphere that receive the converging infrared beam from the beam path, the integrating sphere having a hollow spherical interior, an inlet opening in the integrating sphere which receives the converging beam, an outlet opening in the integrating sphere through which the converging beam passes, a window over the outlet opening on which a sample such as a tablet may be placed in a sample position, and a detector mounted to the integrating sphere to receive infrared radiation reflected from the interior surfaces of the integrating sphere, the interior surfaces of the integrating sphere formed to provide diffuse reflection, whereby infrared reflected from a sample held on the window in sample position will be diffusely reflected in the integrating sphere to the infrared detector mounted to the integrating sphere, and another infrared detector mounted adjacent to the sample position above the window to receive infrared radiation passed through the outlet opening of the integrating sphere, the window, and a sample held in the sample position, to detect infrared transmitted through the sample.

50. The spectrometer system of claim 49 further including a shield mounted at the sample position between the integrating sphere and the detector that detects the infrared transmitted through the outlet opening of the integrated sphere and through the sample, the shield having an inner periphery conforming to the outer periphery of a tablet to be supported on the window above the integrating sphere, the shield blocking infrared radiation, thereby substantially blocking infrared radiation from passing around the lateral periphery of a tablet held at the sample position above the outlet opening of the integrating sphere.

51. The spectrometer system of claim 50 wherein the shield comprises an elastomer pad having an interior opening therein with an inner periphery sized to conform to the outer periphery of the tablet to be held to resiliently engage the outer periphery of the tablet to block off infrared radiation from passing around the pill.

52. The spectrometer system of claim 50 wherein the shield comprises an adjustable iris, the diameter of the inner periphery of which can be adjusted to engage the outer periphery of a circular tablet held at the sample position and supported on the window above the outlet opening of the integrating sphere, the adjustable iris when engaged with a tablet blocking infrared radiation from passing around the periphery of the tablet to the infrared detector mounted to receive infrared radiation transmitted through the tablet.

53. The spectrometer system of claim 52 including an elevational adjustment ring to which the adjustable iris is mounted, the elevational adjustment ring operable by an operator to adjust the height of the inner periphery of the iris above the window to engage against the outer periphery of a tablet.

54. The spectrometer system of claim 49 further including a flip panel mounted between the outlet opening of the integrating sphere and the window on which the sample is supported above the outlet opening, the flip panel movable between a position in which the flip panel allows infrared radiation to pass from the outlet opening through the window to a sample held on the window to a position in which the flip panel blocks the infrared radiation from passing through the window to the sample, the surface of the flip panel facing the outlet opening of the integrating sphere having an infrared reflective surface such that when the flip panel blocks the outlet opening infrared radiation incident thereon will be reflected into the integrating sphere and be detected by the detector mounted in the integrating sphere to allow calibration of the infrared beam provided on the branch beam path to the integrating sphere.

55. An infrared spectrometer system comprising:
(a) a source of infrared radiation which provides a beam of infrared;
(b) an interferometer which receives the beam from the source and produces a modulated output beam;
(c) an infrared detector;
(d) optical elements transmitting the modulated output beam from the interferometer on a beam path including an optical fiber supply cable leading to a probe, a focussing lens for focussing a beam in the beam path into the optical fiber supply cable, the probe having a probe tip at which the supply cable terminates at an outlet end at which infrared is projected, an optical fiber return cable having an inlet end at the probe tip adjacent to the outlet end of the optical fiber supply cable and extending to the infrared detector and that transmits infrared radiation that has been reflected from a sample and received at the inlet end of the return cable to the infrared detector, wherein the probe includes an elongated tubular portion at one end of which is mounted the probe tip; and
(e) a plastic sheath fitted over the elongated tube portion of the probe to protect the probe tube and probe tip from contamination and having an end panel at the tip which is formed to be essentially transparent to infrared.

* * * * *

UNITED STATES PATENT AND TRADEMARK OFFICE
CERTIFICATE OF CORRECTION

PATENT NO. : 6,667,808 B2  
DATED : December 23, 2003  
INVENTOR(S) : Clermont et al.

It is certified that error appears in the above-identified patent and that said Letters Patent is hereby corrected as shown below:

<u>Title page,</u>
Item [*] Notice:, should read:
-- Subject to any disclaimer, the term of this patent is extended or adjusted under 35 U.S.C. 154(b) by 144 days. --

Signed and Sealed this

Seventeenth Day of February, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,667,808 B2  Page 1 of 1
DATED : December 23, 2003
INVENTOR(S) : Todd R. Clermont et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154 (b) by 144 days. --

Column 17,
Line 4, "element" should be -- elements --.
Line 16, "an" should be -- and --.

Column 20,
Line 16, "a round" should be -- around --.

Column 22,
Line 1, "undetected" should be -- undeflected --.

Column 24,
Line 43, "claim 39" should be -- claim 37 --.

Column 25,
Line 28, -- a -- should be inserted before "converging".
Line 39, "an" should be -- and --.

Column 26,
Line 58, -- a -- should be inserted before "sample".

Signed and Sealed this

Nineteenth Day of October, 2004

JON W. DUDAS
*Director of the United States Patent and Trademark Office*